(12) United States Patent
Benam

(10) Patent No.: US 11,679,093 B2
(45) Date of Patent: Jun. 20, 2023

(54) 2-NAPHTHIMIDAMIDES, ANALOGUES THEREOF, AND METHODS OF TREATMENT USING SAME

(71) Applicant: THE REGENTS OF THE UNIVERSITY OF COLORADO, A BODY CORPORATE, Denver, CO (US)

(72) Inventor: Kambez Hajipouran Benam, Denver, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 147 days.

(21) Appl. No.: 17/251,070

(22) PCT Filed: Jun. 11, 2019

(86) PCT No.: PCT/US2019/036499
§ 371 (c)(1),
(2) Date: Dec. 10, 2020

(87) PCT Pub. No.: WO2019/241213
PCT Pub. Date: Dec. 19, 2019

(65) Prior Publication Data
US 2021/0251942 A1    Aug. 19, 2021

Related U.S. Application Data

(60) Provisional application No. 62/683,480, filed on Jun. 11, 2018.

(51) Int. Cl.
| | |
|---|---|
| C07C 257/18 | (2006.01) |
| A61K 31/167 | (2006.01) |
| A61K 31/472 | (2006.01) |
| A61K 31/4725 | (2006.01) |
| C07D 217/26 | (2006.01) |
| C07D 217/12 | (2006.01) |
| A61K 31/245 | (2006.01) |
| A61K 31/194 | (2006.01) |
| A61K 31/195 | (2006.01) |
| A61K 31/4166 | (2006.01) |
| A61K 31/42 | (2006.01) |
| A61K 31/422 | (2006.01) |
| A61K 45/06 | (2006.01) |
| C07C 279/18 | (2006.01) |
| C07D 233/70 | (2006.01) |
| C07D 261/08 | (2006.01) |

(52) U.S. Cl.
CPC .......... *A61K 31/245* (2013.01); *A61K 31/167* (2013.01); *A61K 31/194* (2013.01); *A61K 31/195* (2013.01); *A61K 31/4166* (2013.01); *A61K 31/42* (2013.01); *A61K 31/422* (2013.01); *A61K 45/06* (2013.01); *C07C 257/18* (2013.01); *C07C 279/18* (2013.01); *C07D 233/70* (2013.01); *C07D 261/08* (2013.01)

(58) Field of Classification Search
CPC .. C07C 257/18; A61K 31/167; A61K 31/472; A61K 31/4725; C07D 217/26; C07D 217/12
See application file for complete search history.

(56) References Cited

U.S. PATENT DOCUMENTS

| | | |
|---|---|---|
| 5,869,501 A | 2/1999 | Hirayama et al. |
| 6,258,822 B1 | 7/2001 | Geyer et al. |
| 6,284,796 B1 | 9/2001 | Geyer et al. |
| 6,596,754 B1 | 7/2003 | Hara et al. |

OTHER PUBLICATIONS

Wendt, M. D. et al., "Identification of novel binding interactions in the development of potent, selective 2-naphthamidine inhibitors of urokinase. Synthesis, Structural analysis, and SAR of n-phenyl amide 6-substitution", J. Med. Chem. (2004), 47: pp. 303-324. (Year: 2004).*
STN Registry No. 220295-84-1, Entered Date: Mar. 9, 1999 (Year: 1999).*
Yang, Y. and H. Tang, "Aberrant coagulation causes a hyper-inflammatory response in severe influenza pneumonia", Cellular & Molecular Immunology (2016), 13: pp. 432-442. (Year: 2016).*
PubChem CID: 6347167, Jul. 11, 2005.
International Search Report and Written Opinion dated Aug. 28, 2019 for International Application No. PCT/US2019/036499.
Bhongade, et al., "Insight into the Structural Requirements of Urokinase-Type Plasminogen Activator Inhibitors Based on 3D QSAR CoMFN/CoMSIA Models", J. Med. Chem., 49, 2006, 475-489.
Bruncko, et al., "Naphthamidine urokinase plasminogen activator inhibitors with improved pharmacokinetic properties", Bioorganic & Medicinal Chemistry Letters, 15, 2005, 93-98.
Hosoya, et al., "Effects of Protease Inhibitors on Replication of Various Myxoviruses", Antimicrobial Agents and Chemotherapy, vol. 36, No. 7, Jul. 1992, 1432-1436.
Someya, et al., "Inhibition of Influenza Virus A/WSN Replication by a Trypsin Inhibitor, 6-Amidino-2-Naphtyhl p-Guanidinobixzo-ate", Biochemical and Biophysical Research Communications, vol. 169, No. 1, May 31, 1990, 148-152.
Wendt, et al., "Identification of Novel Binding Interactions in the Development of Potent, Selective 2-Naphthamidine Inhibitors of Urokinase. Synthesis, Structural Analysis, and SAR of N-Phenyl Amide 6-Substitution", J. Med. Chem., 47, 2004, 303-324.

(Continued)

*Primary Examiner* — Joseph R Kosack
*Assistant Examiner* — Sagar Patel
(74) *Attorney, Agent, or Firm* — Saul Ewing, LLP; Kathryn Doyle; Domingos J. Silva

(57) ABSTRACT

The present invention relates in certain aspects to the discovery of novel 2-naphthimidamide compounds that are capable of binding Type II Transmembrane Serine Proteases (TTSPs). In certain embodiments, the compounds of the invention can be used to treat or prevent Influenza A viral infection in a mammal.

18 Claims, 3 Drawing Sheets

(56) References Cited

OTHER PUBLICATIONS

Wendt, et al., "Interaction with the S1Beta-pocket of urokinase: 8-heterocycle substituted and 6,8-disubstituted 2-naphthamidine urokinase inhibitors", Bioorganic & Medicinal Chemistry Letters, 14, 2004, 3063-3068.

* cited by examiner

2-NAPHTHIMIDAMIDES, ANALOGUES THEREOF, AND METHODS OF TREATMENT USING SAME

CROSS-REFERENCE TO RELATED APPLICATIONS

The present application is a 35 U.S.C. § 371 national phase application from, and claims priority to, International Application No. PCT/US2019/036499, filed Jun. 11, 2019, which claims priority under 35 U.S.C. § 119(e) to U.S. Provisional Application No. 62/683,480, filed Jun. 11, 2018, all of which applications are incorporated by reference herein in their entireties.

BACKGROUND OF THE INVENTION

Influenza A virus (IAV) is a major respiratory pathogen that causes significant morbidity and mortality in millions of people every year worldwide. The threat of a highly pathogenic influenza outbreak or pandemic, particularly for high-risk groups (e.g. diabetics, infants, immunocompromised patients, and those suffering chronic inflammatory diseases like asthma and chronic obstructive pulmonary disease, also known as COPD) is eminent. Viral capsid-targeted antiviral therapeutics and vaccination remain the leading strategies used to control influenza infections. However, the rapid emergence of drug-resistant viral mutants (due to new antigenic drifts, or new cross-species strains, e.g., humans and pigs, humans and birds, and so forth), drug toxicities, and the need for annual updating of vaccines based on viral strain, often limit efficacy of these approaches.

Influenza viral particles exhibit three major sub-viral components: an envelope, an intermediate layer, and a core. The envelope is a lipid bilayer with a mosaic structure and contains three transmembrane proteins: hemagglutinin (HA), neuraminidase (NA), and matrix protein 2 (M2). Hemagglutinin is a rod-shaped trimer of three identical subunits, the predominant viral envelope glycoprotein, and serves two key functions: 1) to bind sialic acid receptors on the surface of host cells—primarily respiratory epithelium, and 2) to facilitate virus fusion with host endosomal membranes following receptor-mediated internalization. Activation of HA to support viral infectivity requires extensive conformational changes in the protein that is crucially dependent on cleavage of each of the three HA subunit precursors (HA0 conversion to HA1 & HA2). For most HA subtypes (1-16), there is only one single site of cleavage—an arginine amino acid residue. This cleavage likely occurs outside the host cell by an as yet unidentified enzyme or on the cell surface or intracellularly; viruses with un-cleaved HA are unable to infect the target cells.

Type II Transmembrane Serine Proteases (TTSPs) are a recently characterized family of 17 proteins that are anchored to the cell membrane, and thus unlike other secreted serine proteases. A study, wherein cells were transfected with two human TTSPs that are known to localize to the respiratory tract—Transmembrane Protease Serine 2 (TMPRSS2) and TMPRSS11D (also known as Human Airway Trypsin-like protease [HAT]), showed for the first time and suggested proteolytic activation of HA by airway epithelial cells (Bottcher, et al., 2006, J. Virol. 80(19):9896-8). Since then, there has been growing interest in HA-activating host serine proteases.

Nafamostat (6-carbamimidoylnaphthalen-2-yl 4-guanidinobenzoate), a synthetic pan-serine protease inhibitor that is used clinically as an intravascular anticoagulant, has been shown to exhibit antiviral activity in fully differentiated mucociliated bronchiolar epithelium (a major target tissue for IAV) isolated from multiple human donors when tested in an in vitro IAV infection assay. Nafamostat is a broad-spectrum pan-serine protease inhibitor and may target transmembrane protease serine 11E (DESC1; also known asTMPRSS11E)—one of the least characterized members of the TTSPs family, amongst other proteases. DESC1 is constitutively expressed by healthy-derived and diseased-derived (e.g., cells obtained from patients suffering COPD) primary human lung airway epithelial cells and its transient overexpression in normal bronchial epithelial cells results in an over 80-fold increase in IAV release (virus shedding—i.e. productive infection of the target cells) following pathogenic challenge.

However, nafamostat is not ideal for treating influenza infection for at least two important reasons. As discussed, nafamostat is a broad-spectrum pan-serine protease inhibitor, and its non-specific protease inhibition can cause serious off-target effects in a patient. Additionally, the ester linkage in nafamostat is vulnerable to cleavage, thereby shortening the half-life of the compound in vivo.

There remains a need in the art for compounds and methods of treating and/or preventing influenza A in patients in need thereof. In certain embodiments, such compounds should be useful to treat various strains of influenza infection, such as for example drug-resistant viral mutants. The present invention meets these needs.

BRIEF SUMMARY OF THE INVENTION

The invention provides a compound of Formula (I), or a salt, solvate, enantiomer, diastereoisomer, or tautomer thereof:

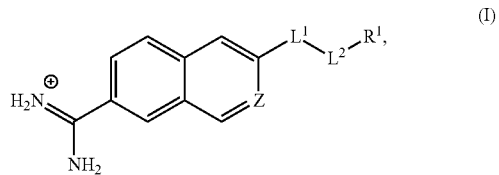

wherein $L^1$, $L^2$, Z, and $R^1$ are defined elsewhere herein. Further, the invention provides pharmaceutical compositions comprising at least one compound of Formula (I).

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

DETAILED DESCRIPTION OF THE INVENTION

Figure 1:
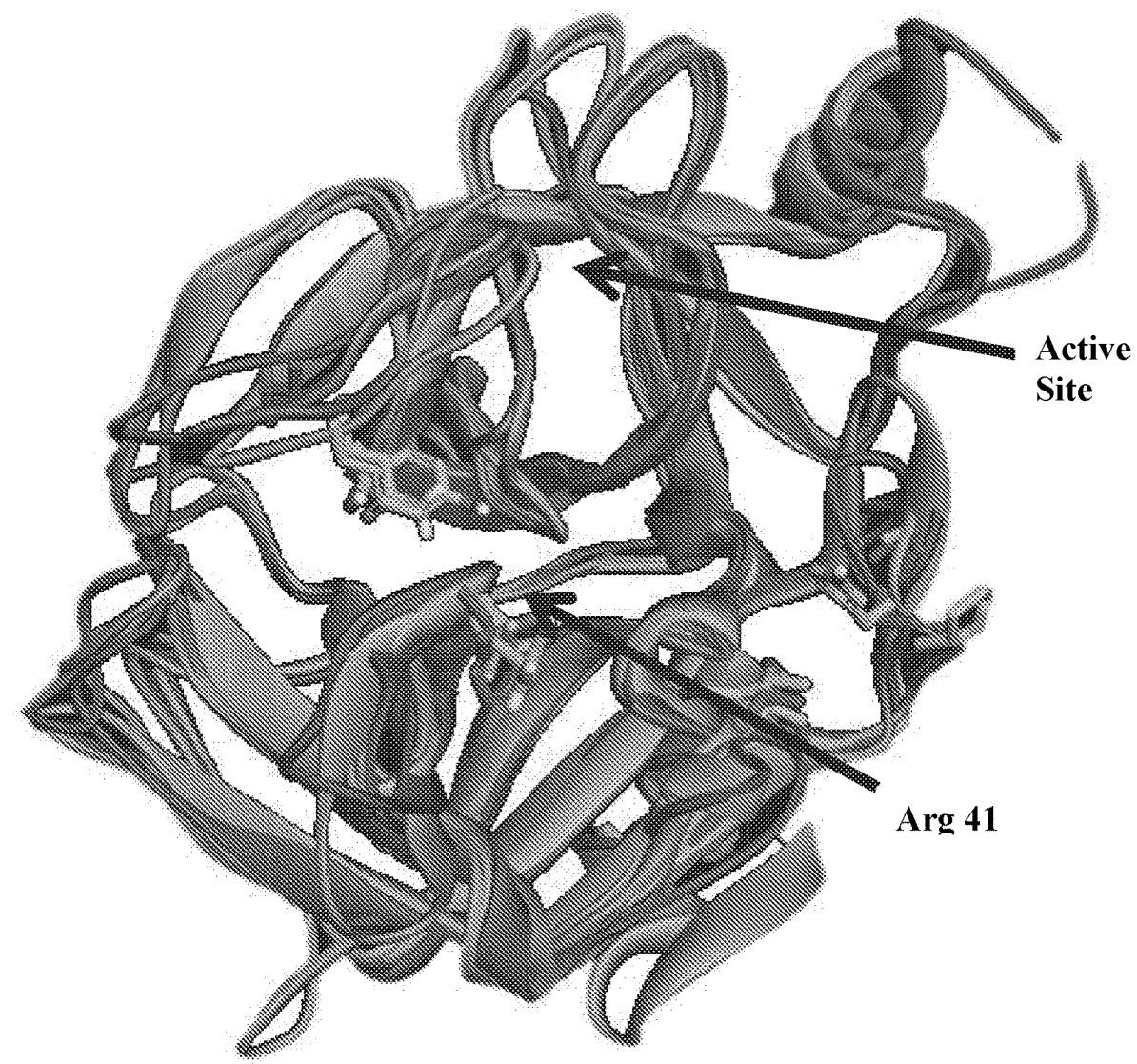
FIG. 1 is an overlaid diagram showing the structures of DESC1, Hepsin, Matripase, Beta-Tryptase and Urokinase. The enzymatic active site and a highly non-conserved residue are highlighted. In DESC1, the highly non-conserved residue is Arg41. This residue was found to be a potential location of interest for selectively inhibiting DESC1, while not inhibiting the other similar proteins.

The present invention relates to the discovery of novel 2-naphthimidamide compounds that can inhibit Type II Transmembrane Serine Proteases (TTSPs). In certain embodiments, the compounds of the invention can be used to treat or prevent Influenza A viral infection in a subject. In other embodiments, the compounds inhibit DESC1 selectively over other transmembrane proteases. In yet other embodiments, the compounds have a therapeutically effective in vivo half-life, allowing for effective treatment of Influenza A in the subject.

Compounds

In one aspect, the invention provides a 2-naphthimidamide compound, or a salt, solvate, enantiomer, diastereoisomer, or tautomer thereof, which is capable of inhibiting human DESC1 protein.

In certain embodiments, the invention provides a compound of Formula (I) or a salt, solvate, enantiomer, diastereoisomer, or tautomer thereof:

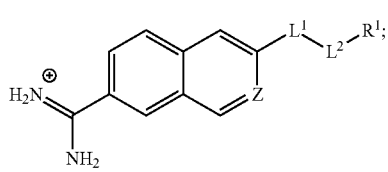

(I)

wherein:
$L^1$ is selected from the group consisting of a bond (i.e., absent),

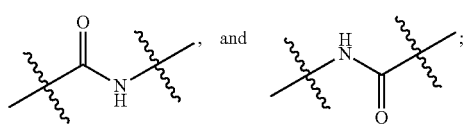 [SMILES: *NC(*)=O ; *NC(*)=O]

$L^2$ is selected from the group consisting of a bond (i.e., absent) and $C_1$-$C_6$ alkylene;
$R^1$ is selected from the group consisting of

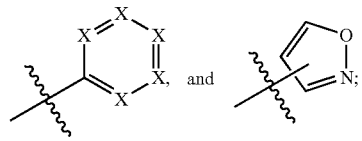

Z is selected from the group consisting of CH and N;
each instance of X is independently selected from the group consisting of $CR^2$ and N, with the proviso that 0-2 instances of X are N;
each instance of $R^2$ is independently selected from the group consisting of H, —CN, —OH, —NRR, F, Cl, Br, I, optionally substituted $C_{1-6}$ alkyl, optionally substituted $C_{1-6}$ alkoxy, optionally substituted $C_{3-8}$ cycloalkyl, optionally substituted phenyl, optionally substituted heteroaryl, optionally substituted heterocyclyl, —(CH$_2$)$_{0-3}$C(=O)OR, —(CH$_2$)$_{0-3}$C(=O)NRR, —(CH$_2$)$_{0-3}$NRRR, and —N(R)—C(=N$^+$RR)—NRR (such as, but not limited to, guanidinium or —NH—C(=N$^+$H$_2$)—NH$_2$); and
each occurrence of R is independently selected from the group consisting of H and $C_1$-$C_6$ alkyl.

In certain embodiments, $L^1$ is a bond (i.e., absent). In certain embodiments, $L^1$ is

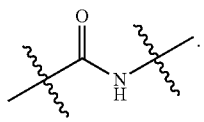

In certain embodiments, $L^1$ is

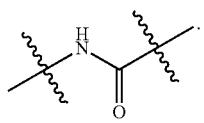

In certain embodiments, $L^2$ is a bond (i.e., absent). In certain embodiments, $L^2$ is $C_1$-$C_6$ alkylene.

In certain embodiments, $R^1$ is

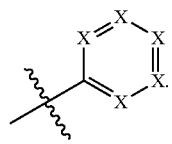

In certain embodiments, $R^1$ is

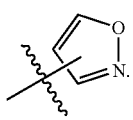

In certain embodiments, Z is CH. In certain embodiments, Z is N.

In certain embodiments, no X is N. In certain embodiments, one X is N. In certain embodiments, two Xs are N.

In certain embodiments, each occurrence of heteroaryl or heterocyclyl is independently selected from the group consisting of pyridyl, pyrimidinyl, pyrazinyl, isoxazolyl, oxazolyl, thiazolyl, imidazolyl, imidazolidin-2-one-1-yl, 1,5-dihydro-2H-imidazol-2-one-1-yl, 2-pyrazolyl, 1,2,3-triazolyl, 1,2,4-triazolyl, uracil, thyminyl, pyranyl, furanyl, and hydantoinyl. In other embodiments, each occurrence of heteroaryl or heterocyclyl is independently optionally substituted.

In certain embodiments, each occurrence of alkyl, alkoxy, cycloalkyl, phenyl, heteroaryl, or heterocyclyl is independently optionally substituted with at least one group selected from the group consisting of —CN, —OR', —NR'R', F, Cl, Br, I, $C_{1-6}$ alkyl, $C_{3-8}$ cycloalkyl, phenyl, heteroaryl, and heterocyclyl, wherein each occurrence of R' is independently selected from the group consisting of H and $C_1$-$C_6$ alkyl.

In certain embodiments, each instance of R² is independently selected from the group consisting of H, —OH, —NH₂, methyl, methoxy,

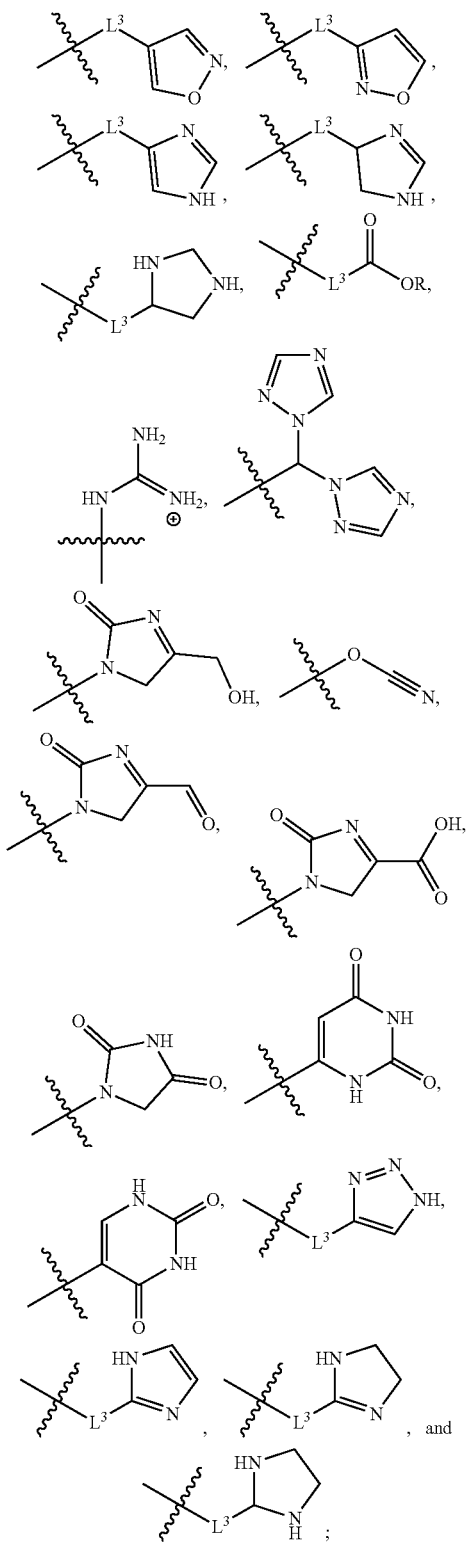

wherein each occurrence of L³ is independently selected from the group consisting of a bond and methylene.

In certain embodiments, one instance of R² is H. In certain embodiments, one instance of R² is —OH. In certain embodiments, one instance of R² is —NH₂. In certain embodiments, one instance of R² is methyl. In certain embodiments, one instance of R² is methoxy. In certain embodiments, one instance of R² is

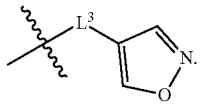

In certain embodiments, one instance of R² is

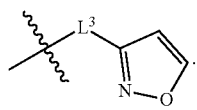

In certain embodiments, one instance of R² is

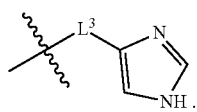

In certain embodiments, one instance of R² is

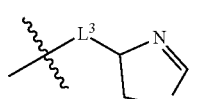

In certain embodiments, one instance of R² is

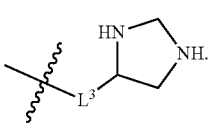

In certain embodiments, one instance of R² is

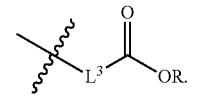

In certain embodiments, one instance of R² is

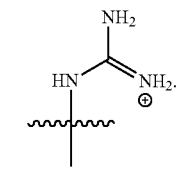

In certain embodiments, one instance of $R^2$ is

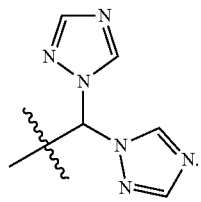 [SMILES: *C(n1cncn1)n1cncn1]

In certain embodiments, one instance of $R^2$ is

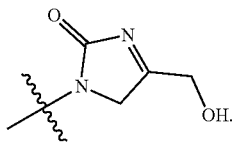 [SMILES: *N1CC(CO)=NC1=O]

In certain embodiments, one instance of $R^2$ is

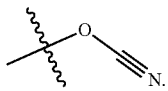 [SMILES: *OC#N]

In certain embodiments, one instance of $R^2$ is

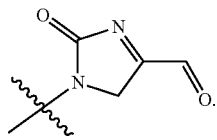 [SMILES: *N1CC(C=O)=NC1=O]

In certain embodiments, one instance of $R^2$ is

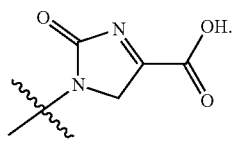 [SMILES: *N1CC(C(=O)O)=NC1=O]

In certain embodiments, one instance of $R^2$ is

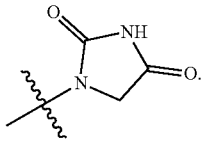 [SMILES: *N1CC(=O)NC1=O]

In certain embodiments, one instance of $R^2$ is

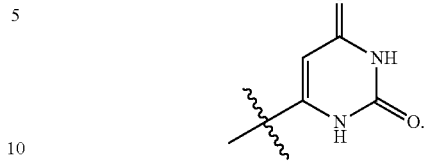

In certain embodiments, one instance of $R^2$ is

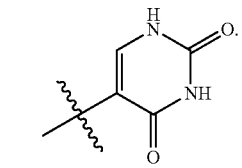 [SMILES: *c1c[nH]c(=O)[nH]c1=O]

In certain embodiments, one instance of $R^2$ is

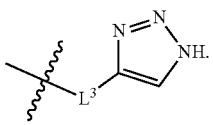

In certain embodiments, one instance of $R^2$ is

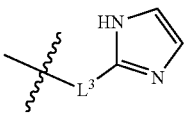

In certain embodiments, one instance of $R^2$ is

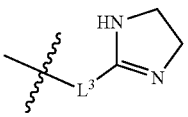

In certain embodiments, one instance of $R^2$ is

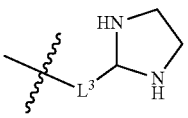

In certain embodiments, one instance of $L^3$ is a bond. In certain embodiments, one instance of $L^3$ is methylene.

In certain embodiments, $R^1$ is phenyl. In certain embodiments, $R^1$ is pyridinyl. In certain embodiments, $R^1$ is pyrimidinyl. In certain embodiments, $R^1$ is isoxazolyl. In certain embodiments, $R^1$ is

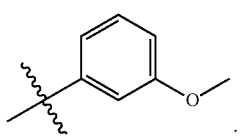 [SMILES: *c1cccc(OC)c1]
In certain embodiments, R¹ is
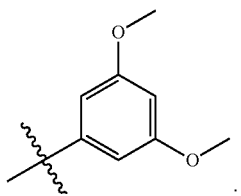 [SMILES: *c1cc(OC)cc(OC)c1]
In certain embodiments, R¹ is
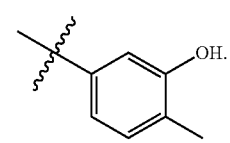 [SMILES: *c1ccc(C)c(O)c1]
In certain embodiments, R¹ is
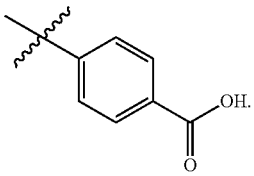 [SMILES: *c1ccc(C(=O)O)cc1]
In certain embodiments, R¹ is
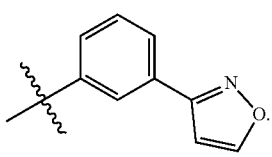 [SMILES: *c1cccc(-c2ccon2)c1]
In certain embodiments, R¹ is
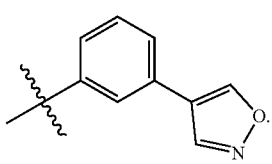 [SMILES: *c1cccc(-c2cnoc2)c1]
In certain embodiments, R¹ is
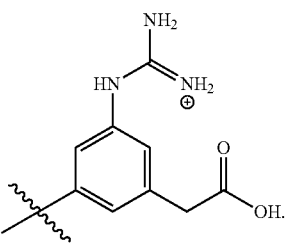 [SMILES: *c1cc(CC(=O)O)cc(NC(N)=[NH2+])c1]
In certain embodiments, R¹ is
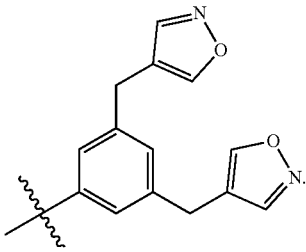 [SMILES: *c1cc(Cc2cnoc2)cc(Cc2cnoc2)c1]
In certain embodiments, R¹ is
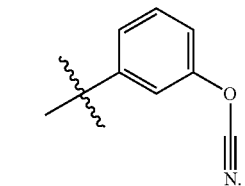
In certain embodiments, R¹ is
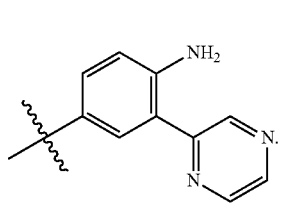 [SMILES: *c1ccc(N)c(-c2cnccn2)c1]
In certain embodiments, R¹ is
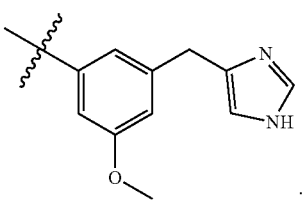 [SMILES: *c1cc(Cc2c[nH]cn2)cc(OC)c1]

In certain embodiments, R¹ is
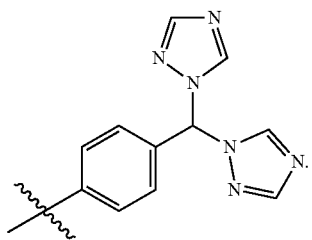 [SMILES: *c1ccc(C(n2cncn2)n2cncn2)cc1]
In certain embodiments, R¹ is
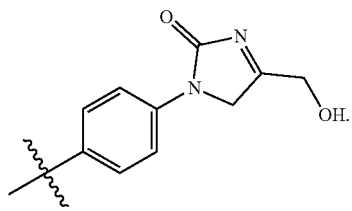 [SMILES: *c1ccc(N2CC(CO)=NC2=O)cc1]
In certain embodiments, R¹ is
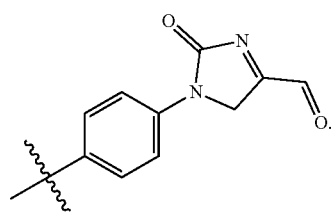 [SMILES: *c1ccc(N2CC(C=O)=NC2=O)cc1]
In certain embodiments, R¹ is
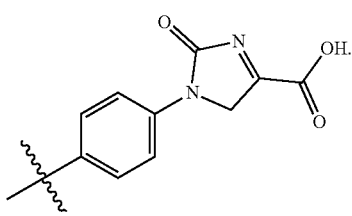 [SMILES: *c1ccc(N2CC(C(=O)O)=NC2=O)cc1]
In certain embodiments, R¹ is
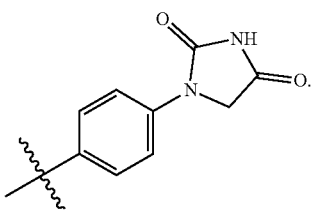 [SMILES: *c1ccc(N2CC(=O)NC2=O)cc1]
In certain embodiments, R¹ is
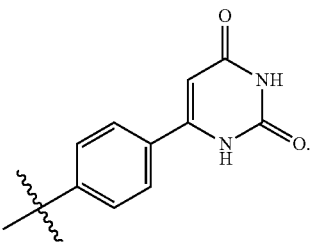 [SMILES: *c1ccc(-c2cc(=O)[nH]c(=O)[nH]2)cc1]
In certain embodiments, R¹ is
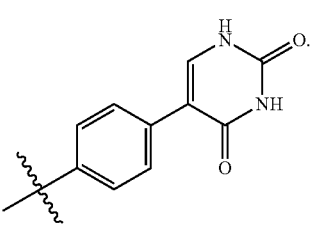 [SMILES: *c1ccc(-c2c[nH]c(=O)[nH]c2=O)cc1]
In certain embodiments, R¹ is
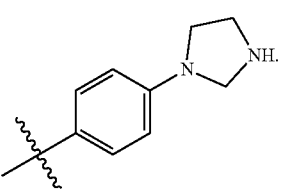 [SMILES: *c1ccc(N2CCNC2)cc1]
In certain embodiments, R¹ is
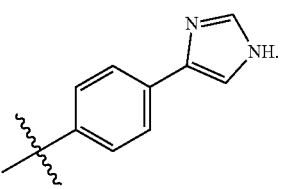 [SMILES: *c1ccc(-c2c[nH]cn2)cc1]
In certain embodiments, R¹ is
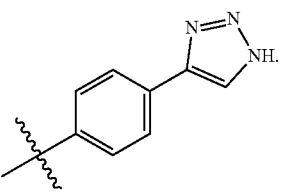 [SMILES: *c1ccc(-c2c[nH]nn2)cc1]

In certain embodiments, R[1] is not

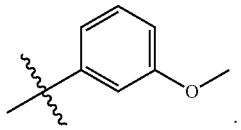 [SMILES: *c1cccc(OC)c1]

In certain embodiments, R[1] is not

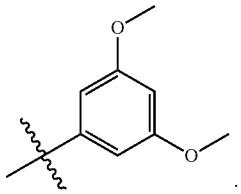 [SMILES: *c1cc(OC)cc(OC)c1]

In certain embodiments, the compound is

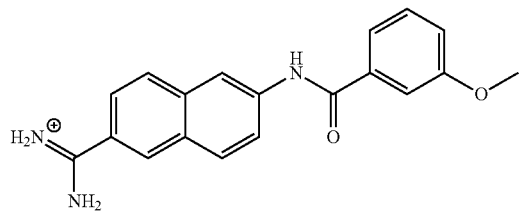 [SMILES: COc1cccc(C(=O)Nc2ccc3cc(C(N)=[NH2+])ccc3c2)c1]

amino(6-(3-methoxybenzamido)naphthalen-2-yl)methaniminium, or a salt or solvate thereof.

In certain embodiments, the compound is

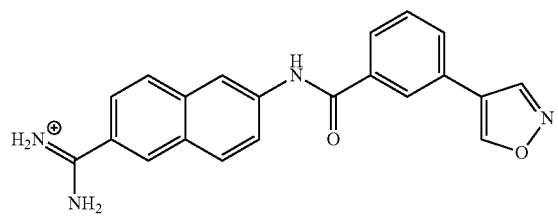 [SMILES: NC(=[NH2+])c1ccc2cc(NC(=O)c3cccc(-c4cnoc4)c3)ccc2c1]

amino(6-(3-(isoxazol-4-yl)benzamido)naphthalen-2-yl)methaniminium, or a salt or solvate thereof. In certain embodiments, the compound is

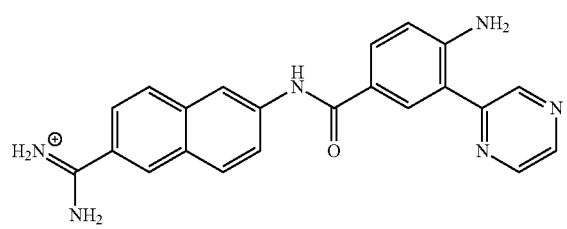 [SMILES: NC(=[NH2+])c1ccc2cc(NC(=O)c3ccc(N)c(-c4cnccn4)c3)ccc2c1]

amino(6-(4-amino-3-(pyrazin-2-yl)benzamido)naphthalen-2-yl)methaniminium, or a salt or solvate thereof. In certain embodiments,

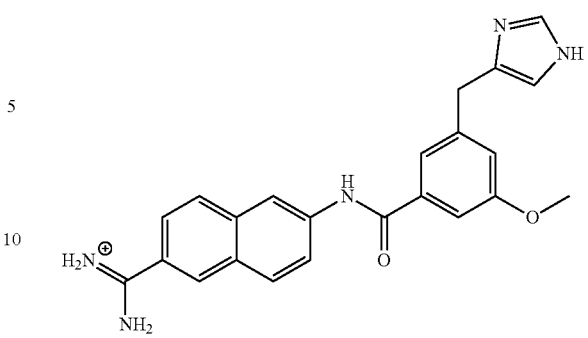

(6-(3-((1H-imidazol-4-yl)methyl)-5-methoxybenzamido)naphthalen-2-yl)(amino)methaniminium, or a salt or solvate thereof. In certain embodiments, the compound is

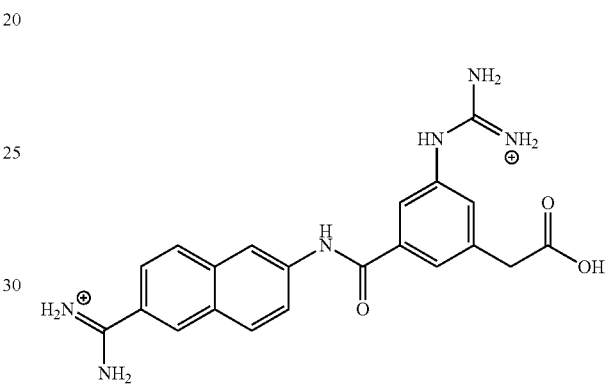

amino(6-(3-((amino(iminio)methyl)amino)-5-(carboxymethyl)benzamido)naphthalen-2-yl)methaniminium, or a salt or solvate thereof. In certain embodiments, the compound is

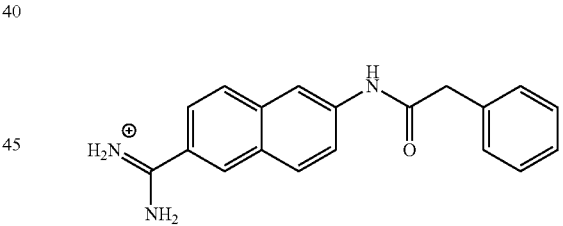

amino(6-(2-phenylacetamido)naphthalen-2-yl)methaniminium, or a salt or solvate thereof. In certain embodiments, the compound is

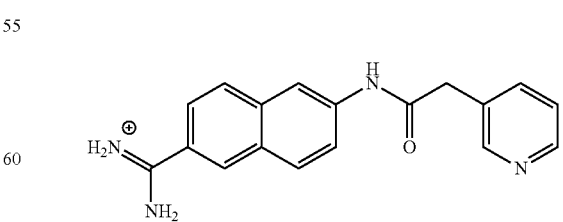

amino (6-(2-(pyridin-3-yl)acetamido)naphthalen-2-yl)methaniminium, or a salt or solvate thereof. In certain embodiments, the compound is

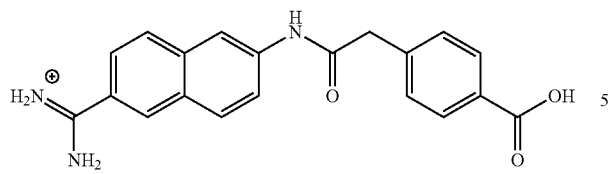

amino(6-(2-(4-carboxyphenyl)acetamido)naphthalen-2-yl)methaniminium, or a salt or solvate thereof. In certain embodiments, the compound is

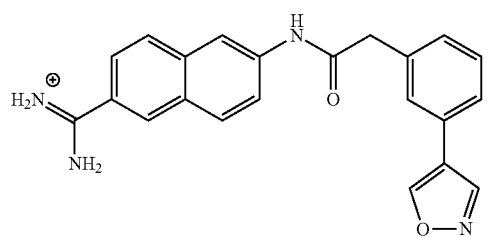 [SMILES: NC(=[NH2+])c1ccc2cc(NC(=O)Cc3cccc(-c4cnoc4)c3)ccc2c1]

amino(6-(2-(3-(isoxazol-4-yl)phenyl)acetamido)naphthalen-2-yl)methaniminium, or a salt or solvate thereof.

In certain embodiments, the compound is

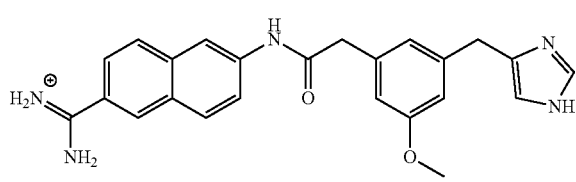 [SMILES: COc1cc(CC(=O)Nc2ccc3cc(C(N)=[NH2+])ccc3c2)cc(Cc2c[nH]cn2)c1]

(6-(2-(3-((1H-imidazol-4-yl)methyl)-5-methoxyphenyl)acetamido)naphthalen-2-yl)(amino)methaniminium, or a salt or solvate thereof. In certain embodiments, the compound is

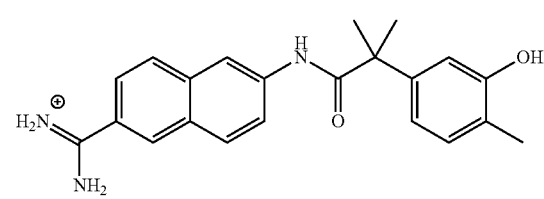 [SMILES: Cc1ccc(C(C)(C)C(=O)Nc2ccc3cc(C(N)=[NH2+])ccc3c2)cc1O]

amino (6-(2-(3-hydroxy-4-methylphenyl)-2-methylpropanamido)naphthalen-2-yl)methaniminium, or a salt or solvate thereof. In certain embodiments, the compound is

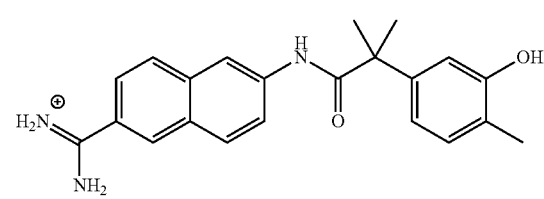 [SMILES: Cc1ccc(C(C)(C)C(=O)Nc2ccc3cc(C(N)=[NH2+])ccc3c2)cc1O]

amino(6-(3-(pyridin-3-yl)propanamido)naphthalen-2-yl)methaniminium, or a salt or solvate thereof. In certain embodiments, the compound is

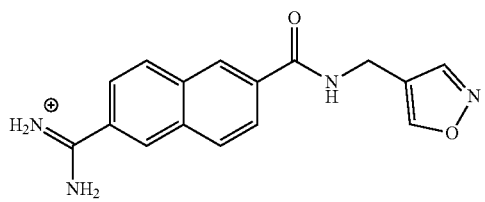 [SMILES: NC(=[NH2+])c1ccc2cc(C(=O)NCc3cnoc3)ccc2c1]

amino(6-((isoxazol-4-ylmethyl)carbamoyl)naphthalen-2-yl)methaniminium, or a salt or solvate thereof. In certain embodiments, the compound is

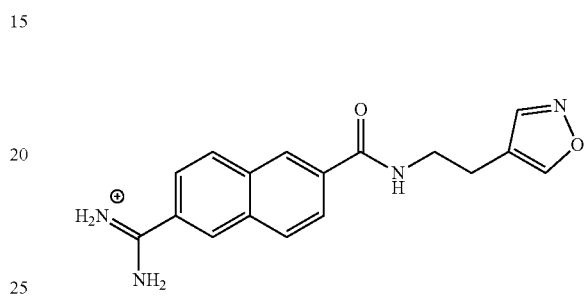

amino(6-((2-(isoxazol-4-yl)ethyl)carbamoyl)naphthalen-2-yl)methaniminium, or a salt or solvate thereof. In certain embodiments, the compound is

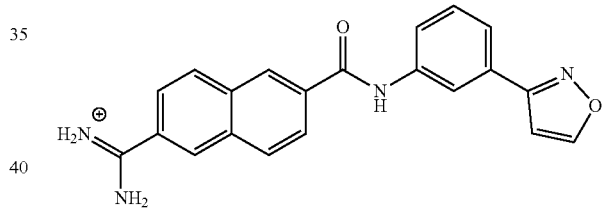

amino(6-((3-(isoxazol-3-yl)phenyl)carbamoyl)naphthalen-2-yl)methaniminium, or a salt or solvate thereof. In certain embodiments, the compound is

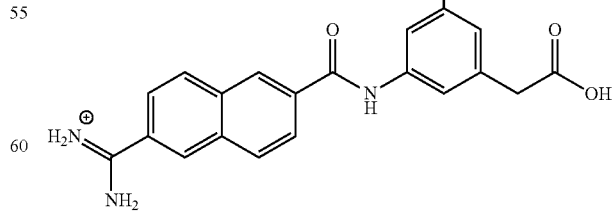

amino((3-(6-(amino(iminio)methyl)-2-naphthamido)-5-(carboxymethyl)phenyl)amino)methaniminium, or a salt or solvate thereof. In certain embodiments, the compound is

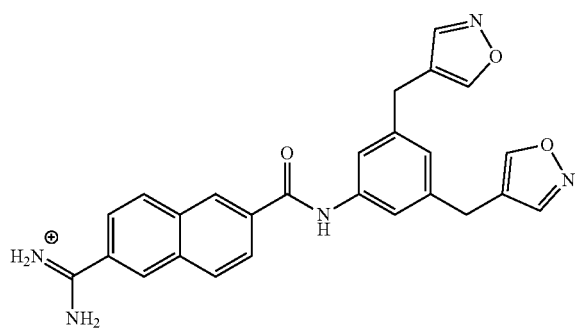 [SMILES: NC(=[NH2+])c1ccc2cc(C(=O)Nc3cc(Cc4cnoc4)cc(Cc4cnoc4)c3)ccc2c1]

amino(6-((3,5-bis(isoxazol-4-ylmethyl)phenyl)carbamoyl)naphthalen-2-yl)methaniminium, or a salt or solvate thereof. In certain embodiments, the compound is

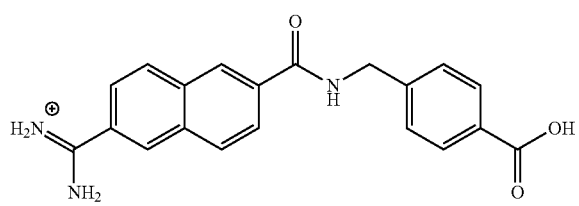 [SMILES: NC(=[NH2+])c1ccc2cc(C(=O)NCc3ccc(C(=O)O)cc3)ccc2c1]

amino(6-((4-carboxybenzyl)carbamoyl)naphthalen-2-yl)methaniminium, or a salt or solvate thereof. In certain embodiments, the compound is

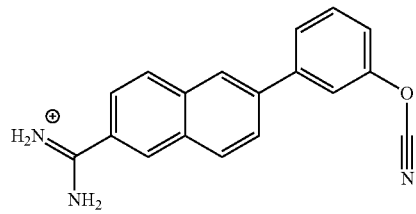 [SMILES: N#COc1cccc(-c2ccc3cc(C(N)=[NH2+])ccc3c2)c1]

amino(6-(3-cyanatophenyl)naphthalen-2-yl)methaniminium, or a salt or solvate thereof. In certain embodiments, the compound is

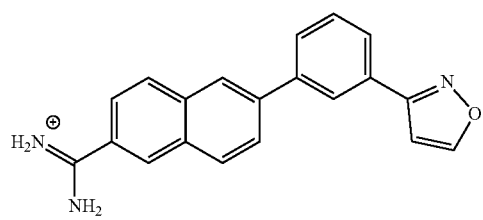

amino(6-(3-(isoxazol-3-yl)phenyl)naphthalen-2-yl)methaniminium, or a salt or solvate thereof. In certain embodiments, the compound is

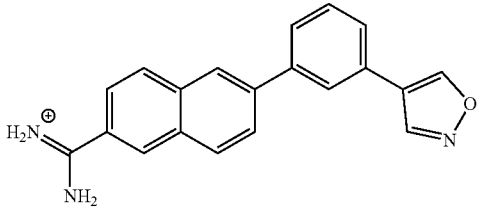

amino(6-(3-(isoxazol-4-yl)phenyl)naphthalen-2-yl)methaniminium, or a salt or solvate thereof. In certain embodiments, the compound is

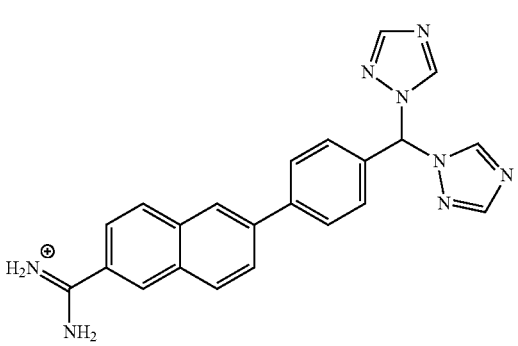 [SMILES: NC(=[NH2+])c1ccc2cc(-c3ccc(C(n4cncn4)n4cncn4)cc3)ccc2c1]

amino(6-(4-(di(1H-1,2,4-triazol-1-yl)methyl)phenyl)naphthalen-2-yl)methaniminium, or a salt or solvate thereof.

In certain embodiments, the compound is

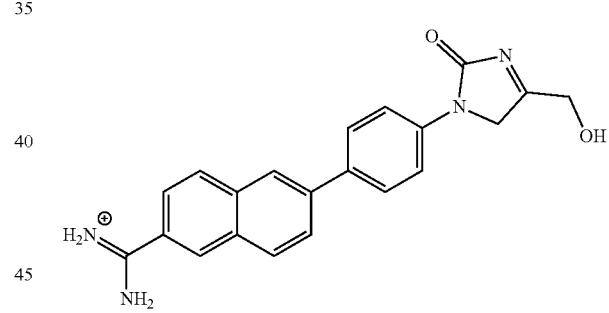

amino(6-(4-(4-(hydroxymethyl)-2-oxo-2,5-dihydro-1H-imidazol-1-yl)phenyl)naphthalen-2-yl)methaniminium, or a salt or solvate thereof. In certain embodiments, the compound is

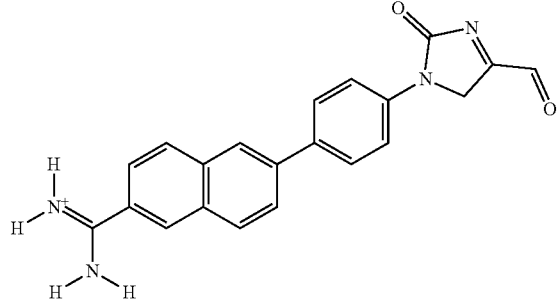

amino(3-(4-(4-(hydroxymethyl)-2-oxo-2,5-dihydro-1H-imidazol-1-yl)phenyl)isoquinolin-7-yl)methaniminium, or a salt or solvate thereof. In certain embodiments, the compound is

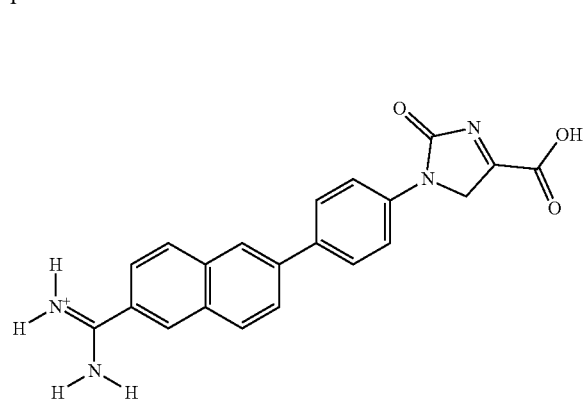

amino(6-(4-(4-carboxy-2-oxo-2,5-dihydro-1H-imidazol-1-yl)phenyl)naphthalen-2-yl)methaniminium, or a salt or solvate thereof. In certain embodiments, the compound is

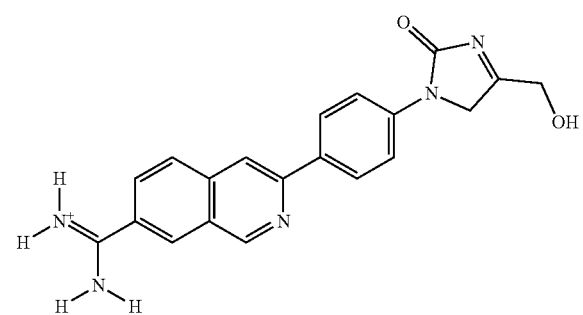 [SMILES: NC(=[NH2+])c1ccc2cc(-c3ccc(N4CC(CO)=NC4=O)cc3)ncc2c1]

amino(3-(4-(4-(hydroxymethyl)-2-oxo-2,5-dihydro-1H-imidazol-1-yl)phenyl)isoquinolin-7-yl)methaniminium, or a salt or solvate thereof. In certain embodiments, the compound is

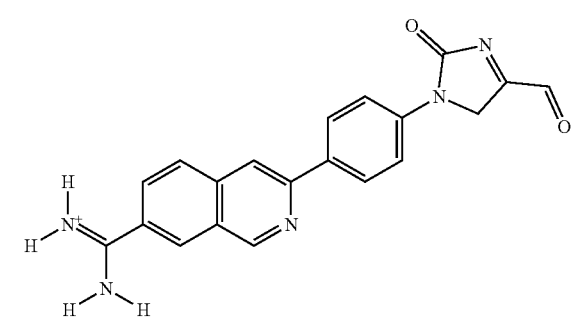

amino(3-(4-(4-formyl-2-oxo-2,5-dihydro-1H-imidazol-1-yl)phenyl)isoquinolin-7-yl)methaniminium, or a salt or solvate thereof. In certain embodiments, the compound is

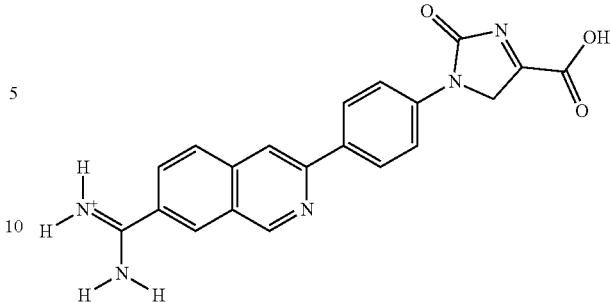

amino(3-(4-(4-carboxy-2-oxo-2,5-dihydro-1H-imidazol-1-yl)phenyl)isoquinolin-7-yl)methaniminium, or a salt or solvate thereof. In certain embodiments, the compound is amino(6-((4-(4-(hydroxymethyl)-2-oxo-2,5-dihydro-1H-imidazol-1-yl)phenyl)carbamoyl)naphthalen-2-yl)methaniminium, or a salt or solvate thereof. In certain embodiments, the compound is amino(3-((4-(4-(hydroxymethyl)-2-oxo-2,5-dihydro-1H-imidazol-1-yl)phenyl)carbamoyl)isoquinolin-7-yl)methaniminium, or a salt or solvate thereof. In certain embodiments, the compound is

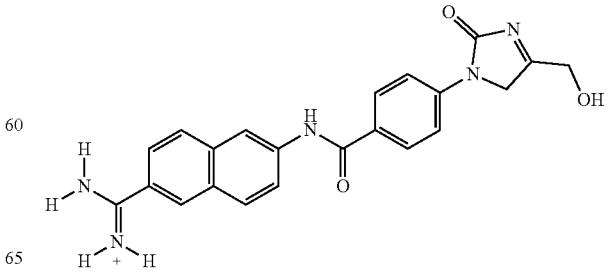

amino(6-(4-(4-(hydroxymethyl)-2-oxo-2,5-dihydro-1H-imidazol-1-yl)benzamido)naphthalen-2-yl)methaniminium, or a salt or solvate thereof. In certain embodiments, the compound is

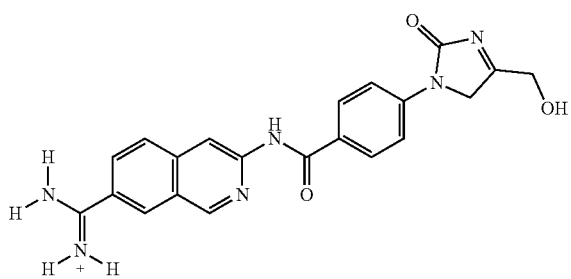

amino(3-(4-(4-(hydroxymethyl)-2-oxo-2,5-dihydro-1H-imidazol-1-yl)benzamido)isoquinolin-7-yl)methaniminium, or a salt or solvate thereof. In certain embodiments, the compound is

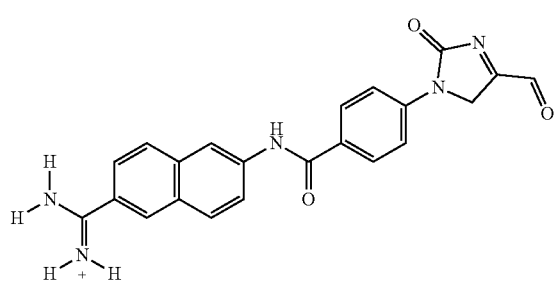

amino(6-(4-(4-formyl-2-oxo-2,5-dihydro-1H-imidazol-1-yl)benzamido)naphthalen-2-yl)methaniminium, or a salt or solvate thereof. In certain embodiments, the compound is

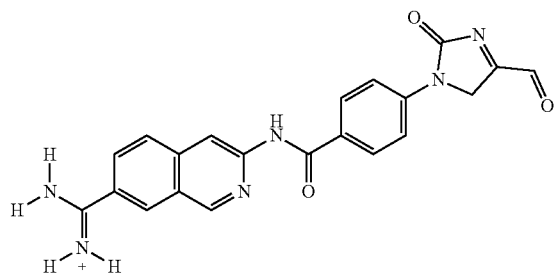

amino(3-(4-(4-formyl-2-oxo-2,5-dihydro-1H-imidazol-1-yl)benzamido)isoquinolin-7-yl)methaniminium, or a salt or solvate thereof. In certain embodiments, the compound is

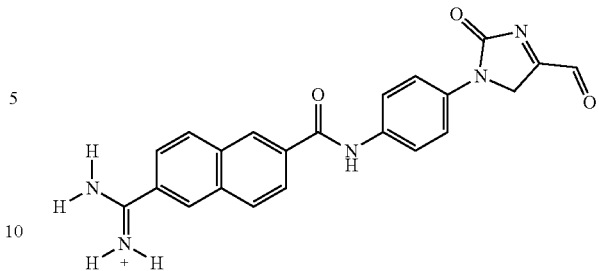

amino(6-((4-(4-formyl-2-oxo-2,5-dihydro-1H-imidazol-1-yl)phenyl)carbamoyl)naphthalen-2-yl)methaniminium, or a salt or solvate thereof. In certain embodiments, the compound is

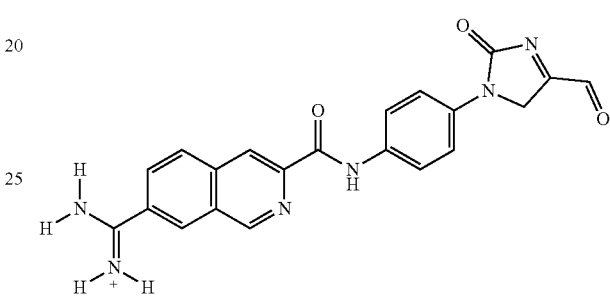

amino(3-((4-(4-formyl-2-oxo-2,5-dihydro-1H-imidazol-1-yl)phenyl)carbamoyl)isoquinolin-7-yl)methaniminium, or a salt or solvate thereof. In certain embodiments, the compound is

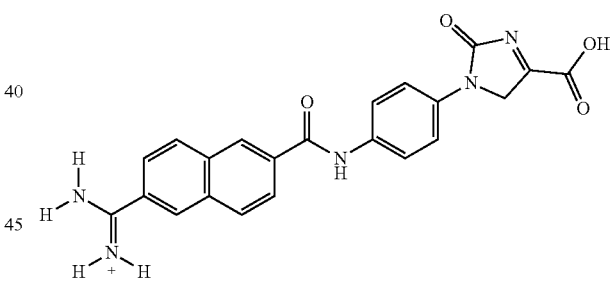

amino(6-((4-(4-carboxy-2-oxo-2,5-dihydro-1H-imidazol-1-yl)phenyl)carbamoyl)naphthalen-2-yl)methaniminium, or a salt or solvate thereof. In certain embodiments, the compound is

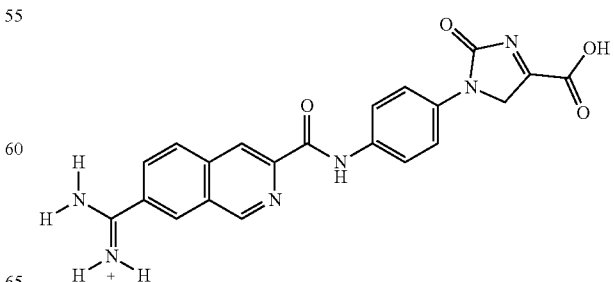

amino(3-((4-(4-carboxy-2-oxo-2,5-dihydro-1H-imidazol-1-yl)phenyl)carbamoyl)isoquinolin-7-yl)methaniminium, or a salt or solvate thereof. In certain embodiments, the compound is

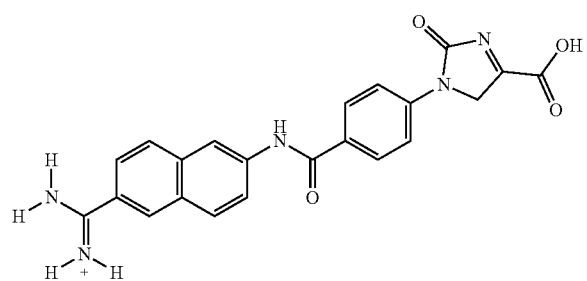

amino(6-(4-(4-carboxy-2-oxo-2,5-dihydro-1H-imidazol-1-yl)benzamido)naphthalen-2-yl)methaniminium, or a salt or solvate thereof. In certain embodiments, the compound is

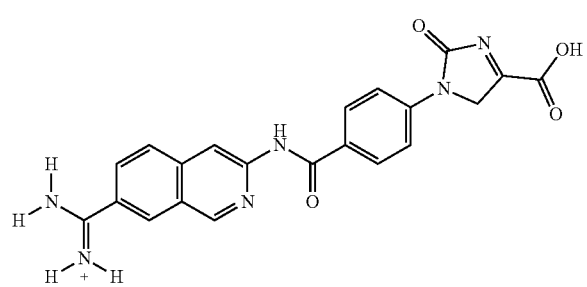

amino(3-(4-(4-carboxy-2-oxo-2,5-dihydro-1H-imidazol-1-yl)benzamido)isoquinolin-7-yl)methaniminium, or a salt or solvate thereof. In certain embodiments, the compound is

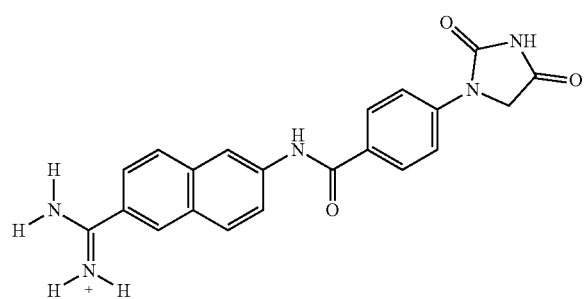

amino(6-(4-(2,4-dioxoimidazolidin-1-yl)benzamido)naphthalen-2-yl)methaniminium, or a salt or solvate thereof. In certain embodiments, the compound is

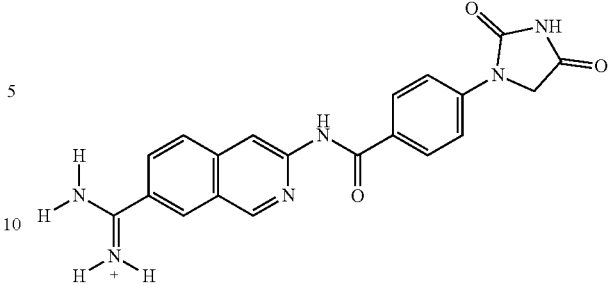

amino(3-(4-(2,4-dioxoimidazolidin-1-yl)benzamido)isoquinolin-7-yl)methaniminium, or a salt or solvate thereof. In certain embodiments, the compound is

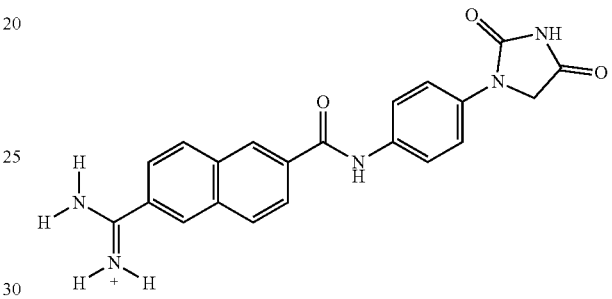

amino(6-((4-(2,4-dioxoimidazolidin-1-yl)phenyl)carbamoyl)naphthalen-2-yl)methaniminium, or a salt or solvate thereof. In certain embodiments, the compound is

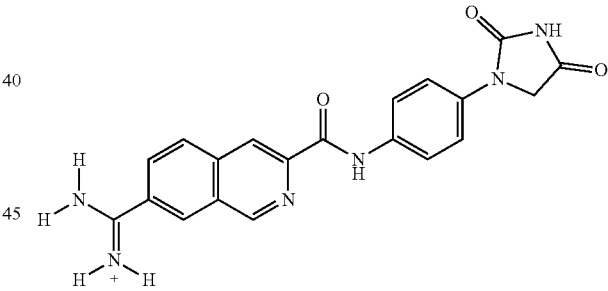

amino(3-((4-(2,4-dioxoimidazolidin-1-yl)phenyl)carbamoyl)isoquinolin-7-yl)methaniminium; or a salt or solvate thereof.

In certain embodiments, the compound is not

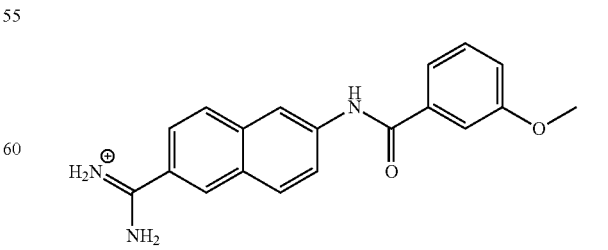

amino(6-(3-methoxybenzamido)naphthalen-2-yl)methaniminium.

In certain embodiments, the compound of the invention is capable of binding at least one Type II Transmembrane Serine Proteases (TTSPs). In other embodiments, the compound of the invention is capable of binding at least one transmembrane protease serine protein selected from the group consisting of transmembrane protease serine 2 (TMPRSS2), transmembrane protease serine 11E (DESC1), transmembrane protease serine 11D (TMPRSS11D, Human Airway Trypsin-like protease [HAT]), and transmembrane protease serine 13 (TMPRSS13, also known as Mosaic Seine Protease Large-form [MSPL]).

In certain embodiments, the compound of the invention is useful in the treatment or prevention of viral infection in a subject in need thereof. In other embodiments, the viral infection is caused by an influenza virus or a coronavirus. In yet other embodiments, the influenza virus is selected from the group consisting of influenza A viruses and influenza B viruses.

In certain embodiments, the influenza A virus is selected from, but not necessarily limited to, the group consisting of hemagglutinin (H1-H17) subtypes, neuraminidase (N1-10) subtypes, and outbreak, epidemic and pandemic strains, including but not limited to H1N1, H3N2, H5N1, and H7N9. In other embodiments, the influenza B virus is at least one selected from, but not necessarily limited to, the group consisting of B/Yamagata and B/Victoria. In yet other embodiments, the coronavirus is selected from the group consisting of, but not limited to Severe Acute Respiratory Syndrome Coronavirus (SARS-CoV), Middle East Respiratory Syndrome Coronavirus (MERS-CoV), Human Coronavirus 229E (HCoV-229E), genotypes A-D of Human Coronavirus OC43 (HCoV-OC43), Human Coronavirus NL63 (HCoV-NL63, New Haven Coronavirus), and Human Coronavirus HKU1 (HCoV-HKU1). In yet other embodiments, the viral infection is caused by influenza A virus (IAV) or influenza B virus (IBV).

In certain embodiments, the viral infection is caused by a virus having hemagglutinin (HA) transmembrane protein. Without intending to be limited to any particular theory, the compound of the invention prevents cleavage of hemagglutinin (HA) in influenza viruses. In other embodiments, the viral infection is treated or prevented by inhibiting the cleavage of HA by at least one TTSP in the subject. In yet other embodiments, the viral infection is treated or prevented by inhibiting DESC1.

In certain embodiments, the viral infection is caused by a cross-species strain of an influenza virus. In other embodiments, the viral infection is also capable of infecting at least one non-human species. In yet other embodiments, the at least one non-human species is a livestock animal.

In certain embodiments, the subject is a mammal or bird. In other embodiments, the subject is a human.

In certain embodiments, the compound is useful in treating or preventing infection from more than one viral pathogen. In other embodiments, the compound is useful in treating or preventing infection from at least two different viral strains.

In certain embodiments, the compound is useful in treating a viral infection such that the treatment does not require annual updates based on viral strain development or evolution, as is the case with many vaccines. In other embodiments, the compound exerts minimal, if any, evolutionary pressure on the viruses being treated or prevented, thereby preventing or reducing the generation of mutant viral strains.

In certain embodiments, the compound of the invention is formulated as part of a pharmaceutical composition, further comprising at least one pharmaceutically acceptable carrier.

In certain embodiments, the pharmaceutical composition further comprises at least one additional therapeutic agent. In other embodiments, the at least one additional therapeutic agent is an antiviral agent. In yet other embodiments, the at least one additional therapeutic agent is an antiviral agent for the treatment of influenza infection.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereoisomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$.

In certain embodiments, isotopically-labeled compounds are useful in drug or substrate tissue distribution studies. Isotopically-labeled compounds are prepared by any suitable method or by processes using an appropriate isotopically-labeled reagent in place of the non-labeled reagent otherwise employed.

The compounds described herein may form salts with acids or bases, and such salts are included in the present invention. In certain embodiments, the salts are pharmaceutically acceptable salts. The term "salts" embraces addition salts of free acids or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hemisulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, O-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Acid addition salts are generally formed by combining the target freebase with a salt former in a solvent, forming a solution, and collecting the salt as a solid. The molar ratio of salt former to free base may vary (e.g., 1:1, 2:1, 1:2, etc.). A ratio of 1:1 may be preferred. Solvents may include, but are not limited to methyl ethyl ketone, methyl isobutyl ketone, ethyl acetate, isopropyl acetate, water, heptane, methyl tert-butyl ether, cyclohexane, toluene, methanol, ethanol, n-propanol, isopropanol, n-butanol, 2-butanol, isoamyl alcohol, tetrahydrofuran and acetonitrile, and mixtures thereof.

Synthesis

The compounds described herein, and other related compounds having different substituents are synthesized using techniques and materials described herein and as described, for example, in Fieser & Fieser's Reagents for Organic Synthesis, Vol. 1-17 (John Wiley and Sons, 1991); Rodd's Chemistry of Carbon Compounds, Vol. 1-5 and Supplementals (Elsevier Science Publishers, 1989); Organic Reactions, Vol. 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry, $4^{th}$ Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein. See, for example, Northen, et al., 2002, J. Chem. Soc., Perkin Trans. 1, 108-115; doi: 10.1039/B102224P.

Definitions

As used herein, each of the following terms has the meaning associated with it in this section.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science, and organic chemistry are those well-known and commonly employed in the art. It should be understood that the order of steps or order for performing certain actions is immaterial, so long as the present teachings remain operable. Moreover, two or more steps or actions can be conducted simultaneously or not.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B."

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

A "disease" as used herein is a state of health of an animal wherein the animal cannot maintain homeostasis, and wherein if the disease is not ameliorated then the animal's health continues to deteriorate.

The terms "patient," "subject" or "individual" are used interchangeably herein, and refer to any animal, or cells thereof whether in vitro or in situ, amenable to the methods described herein. In a non-limiting embodiment, the patient, subject or individual is a human. In other embodiments, the patient is a non-human mammal including, for example, livestock and pets, such as ovine, bovine, porcine, canine, feline and murine mammals. In yet other embodiments, the patient is an avian animal or bird. Preferably, the patient, individual or subject is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that can be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, and/or a symptom of a condition contemplated herein, with the purpose to cure, heal, alleviate, relieve, alter, remedy, ameliorate, improve, or affect a condition contemplated herein and/or the symptoms of a condition contemplated herein. Such treatments may be specifically tailored or modified, based on knowledge obtained from the field of pharmacogenomics.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is ($C_1$-$C_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is ($C_1$-$C_6$)alkyl, such as, but not limited to, ethyl, methyl, isopropyl, isobutyl, n-pentyl, n-hexyl and cyclopropylmethyl.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene.

As used herein, the term "aromatic" refers to a carbocycle or heterocycle with one or more polyunsaturated rings and having aromatic character, i.e. having (4n+2) delocalized ☐(pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl.

As used herein, the term "aryl-($C_1$-$C_6$)alkyl" refers to a functional group wherein a one to six carbon alkanediyl chain is attached to an aryl group, e.g., —$CH_2CH_2$-phenyl or —$CH_2$-phenyl (or benzyl). Specific examples are aryl-$CH_2$— and aryl-$CH(CH_3)$—. The term "substituted aryl-($C_1$-$C_6$)alkyl" refers to an aryl-($C_1$-$C_6$)alkyl functional group in which the aryl group is substituted. A specific example is substituted aryl($CH_2$)—. Similarly, the term "heteroaryl-($C_1$-$C_6$)alkyl" refers to a functional group wherein a one to three carbon alkanediyl chain is attached to a heteroaryl group, e.g., —$CH_2CH_2$-pyridyl. A specific example is heteroaryl-($CH_2$)—. The term "substituted heteroaryl-($C_1$-$C_6$)alkyl" refers to a heteroaryl-($C_1$-$C_6$)alkyl functional group in which the heteroaryl group is substituted. A specific example is substituted heteroaryl-($CH_2$)—.

As used herein, the term "cycloalkyl" by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples of ($C_3$-$C_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—CH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclic and heteroaryl moieties is intended to be representative and not limiting.

As used herein, the term "substituted" refers to that an atom or group of atoms has replaced hydrogen as the substituent attached to another group.

As used herein, the term "substituted alkyl" or "substituted cycloalkyl" refers to alkyl or cycloalkyl, as defined elsewhere herein, substituted by one, two or three substituents independently selected from the group consisting of halogen, —OH, alkoxy, tetrahydro-2-H-pyranyl, —$NH_2$, —$NH(C_1$-$C_6$ alkyl), —$N(C_1$-$C_6$ alkyl)$_2$, 1-methyl-imidazol-2-yl, pyridin-2-yl, pyridin-3-yl, pyridin-4-yl, —C(=O)OH, —C(=O)O($C_1$-$C_6$)alkyl, trifluoromethyl, —C(=O)$NH_2$, —C(=O)NH($C_1$-$C_6$)alkyl, —C(=O)N(($C_1$-$C_6$)alkyl)$_2$, —$SO_2NH_2$, —$SO_2$NH($C_1$-$C_6$ alkyl), —$SO_2$N($C_1$-$C_6$ alkyl)$_2$, —C(=NH)$NH_2$, and —$NO_2$, in certain embodiments containing one or two substituents independently selected from halogen, —OH, alkoxy, —$NH_2$, trifluoromethyl, —N($CH_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic.

Unless otherwise noted, when two substituents are taken together to form a ring having a specified number of ring atoms (e.g., $R^2$ and $R^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual sub-combination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

Ranges: throughout this disclosure, various aspects of the present invention can be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise. This applies regardless of the breadth of the range.

The following abbreviations are used herein: COPD, chronic obstructive pulmonary disease; DESC1, target transmembrane protease serine 11E; HA, hemagglutinin; HAT, Human Airway Trypsin-like protease; IAV, Influenza A virus; IBV, Influenza B virus; M2, matrix protein 2; NA, neuraminidase; TMPRSS2, Transmembrane Protease Serine 2; TTSPs, Type II Transmembrane Serine Proteases.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Computational Studies

Small molecule docking was employed to predict the binding orientations of the small molecules utilizing a combination of Biovia Discovery Studio and YASARA Structure. Top scoring poses for the docked small molecules were then subjected to explicit solvent-based molecular dynamics simulation with the AMBER 14 forcefield using YASARA structure. Refined protein-ligand complexes were then transferred to Biovia Discovery Studio and the binding energies calculated using the Generalized Born with simple SWitching (GBSW) implicit solvent model.

Computational studies were undertaken to determine the binding energies of nafamostat, various nafamostat metabolites and nafamostat analogues with DESC1 protein. Binding was specifically explored in the region proximal to the Arg41 residue in DESC1 (FIG. 1). This residue is not highly conserved amongst proteins related to DESC1, making it an ideal target for selective inhibition of DESC1, while leaving similar proteins, such as hepsin, matripase, beta-tryptase and urokinase, uninhibited.

Figure 2A:
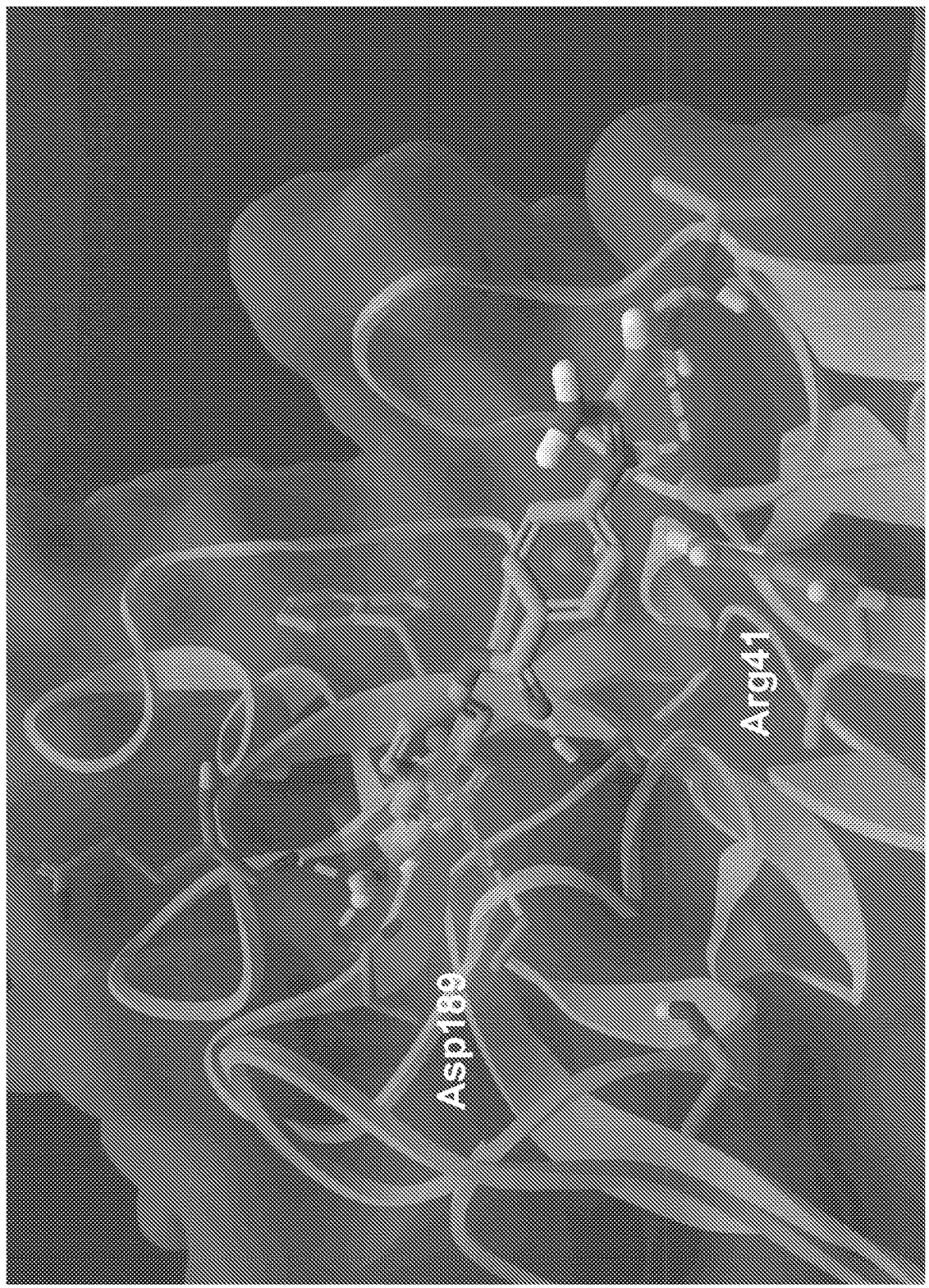
FIGS. 2A-2B are simulated diagrams showing the nafamostat binding mode in the Arg41-Asp189 pocket of DESC1. Binding energy and ligand efficiency calculations were conducted based on binding of certain compounds in this binding pocket.
Figure 2B:
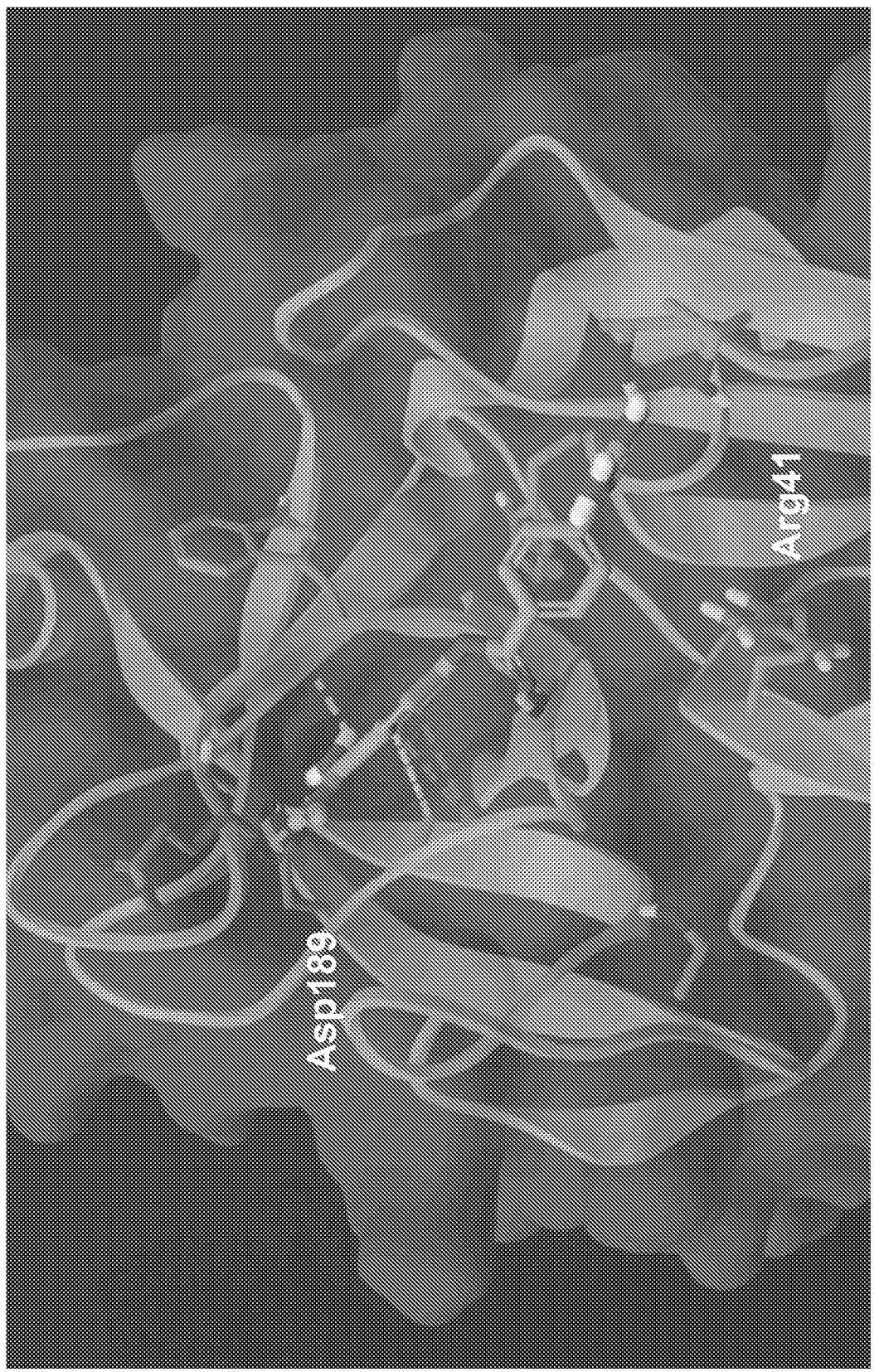

Predictive binding calculations of nafamostat to DESC1 were found to be consistent with binding modes observed in crystal structures of other protease inhibitors (FIGS. 2A-2B). The binding calculations showed characteristic ionic/H-bonding interactions between amidine and Asp189 as well as pi-stacking with nafamostat's naphthamidine moiety. H-bond interactions between nafamostat's guanidinium group and the Thr61/Thr62 residues were also observed, as well as interaction with the backbone carbonyl of the Cys58 residue at the opposite end of the binding pocket.

Because nafamostat contains an ester linkage that can be readily cleaved by esterases highly expressed in the gut and blood under in vivo conditions, the binding energies of the metabolites of nafamostat were also determined.

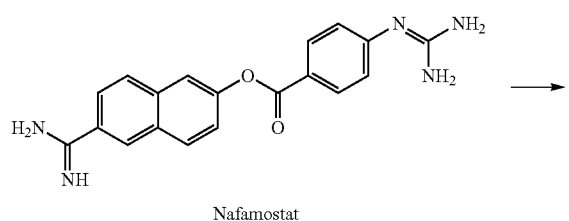

Nafamostat

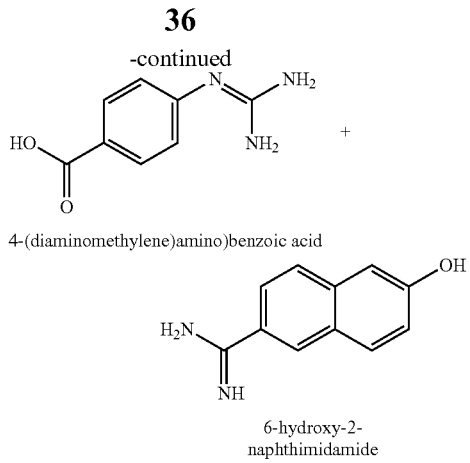

4-(diaminomethylene)amino)benzoic acid 6-hydroxy-2-naphthimidamide

TABLE 1

| Compound | Binding Energy (kcal/mol) | Ligand Efficiency* (kcal mol$^{-1}$ atom$^{-1}$) |
|---|---|---|
| Nafamostat | −10.5 | 0.40 |
| 4-((diaminomethylene)amino)benzoic acid | −7.2 | 0.55 |
| 6-hydroxy-2-naphthimidamide | −7.6 | 0.55 |

*Ligand Efficiency = Binding Energy/# of heavy atoms

In order to prevent potential esterase breakdown of the inhibitors, compounds having amide linkages were explored. Compounds of the invention were found to have better binding energy and ligand efficiency values for DESC1 binding than those calculated for nafamostat. Additionally, nafamostat and compounds of the invention were similarly used in binding calculations with Hepsin, a close relative of DESC1 protein, to determine selectivity.

TABLE 2

| Compound | BE (kcal/mol) DESC1/Hepsin | LE (kcal mol$^{-1}$ atom$^{-1}$) DESC1/Hepsin |
|---|---|---|
| Nafamostat | −10.5/−10.4 | 0.40/0.40 |
|  | −12.7/−9.9 | 0.47/0.37 |

TABLE 2-continued

| Compound | BE (kcal/mol) DESC1/Hepsin | LE (kcal mol⁻¹ atom⁻¹) DESC1/Hepsin |
|---|---|---|
| (structure) | −11.9/−9.6 | 0.45/0.37 |
| (structure) | −11.9/−9.7 | 0.45/0.37 |
| (structure) | −11.1/−9.6 | 0.37/0.32 |
| (structure) | −11.1/−10.4 | 0.37/0.37 |
| (structure) | −10.8/−9.9 | 0.40/0.37 |
| (structure) | −10.7/−9.3 | 0.47/0.40 |

TABLE 2-continued

| Compound | BE (kcal/mol) DESC1/Hepsin | LE (kcal mol$^{-1}$ atom$^{-1}$) DESC1/Hepsin |
|---|---|---|
| 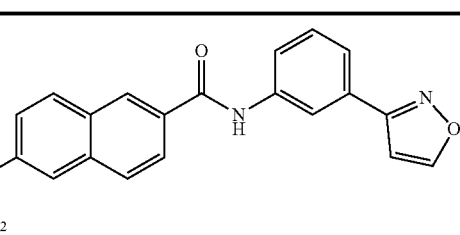 | −10.6/−9.3 | 0.47/0.40 |
| 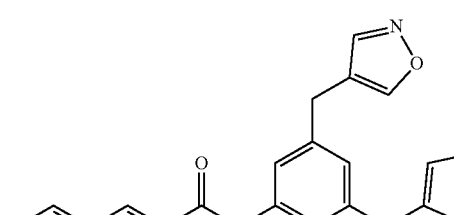 | −10.5/−9.8 | 0.31/0.29 |
| 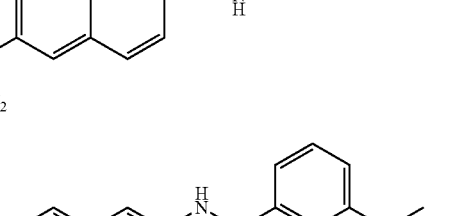 | −10.1/−9.4 | 0.42/0.39 |

Enumerated Embodiments

The following exemplary embodiments are provided, the numbering of which is not to be construed as designating levels of importance.

Embodiment 1 provides a compound of Formula (I), or a salt, solvate, enantiomer, diastereoisomer, or tautomer thereof:

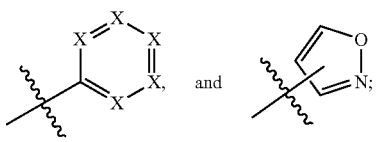

(I)

wherein: L$^1$ is selected from the group consisting of a bond (absent),

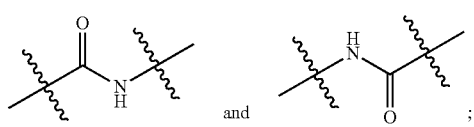 [SMILES: *NC(*)=O ; *NC(*)=O]

and

L$^2$ is selected from the group consisting of a bond (absent) and C$_1$-C$_6$ alkylene; R$^1$ is selected from the group consisting of

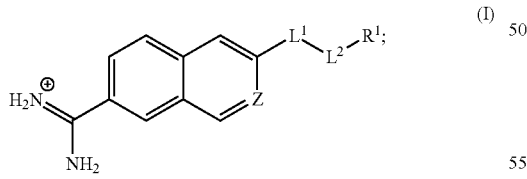

Z is selected from the group consisting of CH and N; each instance of X is independently selected from the group consisting of CR$^2$ and N, with the proviso that 0-2 instances of X are N; and each instance of R$^2$ is independently selected from the group consisting of H, —CN, —OH, —NRR, F, Cl, Br, I, optionally substituted C$_{1-6}$ alkyl, optionally substituted C$_{1-6}$ alkoxy, optionally substituted C$_{3-8}$ cycloalkyl, optionally substituted phenyl, optionally substituted heteroaryl, optionally substituted heterocyclyl, —(CH$_2$)$_{0-3}$C(=O)OR, —(CH$_2$)$_{0-3}$C(=O)NRR, —(CH$_2$)$_{0-3}$NRRR, and —N(R)—C(=N$^+$RR)—NRR; and each occurrence of R is independently selected from the group consisting of H and C$_1$-C$_6$ alkyl, wherein the compound is not amino(6-(3-methoxybenzamido)naphthalen-2-yl)methaniminium.

Embodiment 2 provides a compound of Embodiment 1, wherein each occurrence of heteroaryl or heterocyclyl is independently selected from the group consisting of pyridyl, pyrimidinyl, pyrazinyl, isoxazolyl, oxazolyl, thiazolyl, imidazolyl, imidazolidin-2-one-1-yl, 1,5-dihydro-2H-imidazol-2-one-1-yl, 2-pyrazolyl, 1,2,3-triazolyl, 1,2,4-triazolyl, uracil, thyminyl, pyranyl, furanyl, and hydantoinyl.

Embodiment 3 provides a compound of any of Embodiments 1-2, wherein each occurrence of alkyl, alkoxy, cycloalkyl, phenyl, heteroaryl, or heterocyclyl is independently optionally substituted with at least one group selected from the group consisting of —CN, —OR', —NR'R', F, Cl, Br, I, $C_{1-6}$ alkyl, $C_{3-8}$ cycloalkyl, phenyl, heteroaryl, and heterocyclyl, wherein each occurrence of R' is independently selected from the group consisting of H and $C_1$-$C_6$ alkyl.

Embodiment 4 provides a compound of any of Embodiments 1-3, wherein each instance of $R^2$ is independently selected from the group consisting of H, —OH, —NH₂, methyl, methoxy,

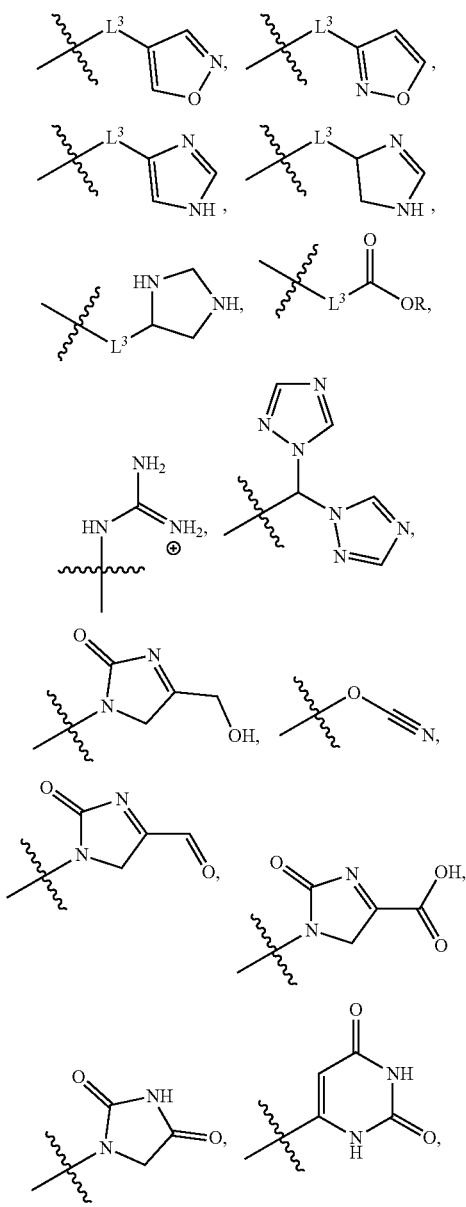

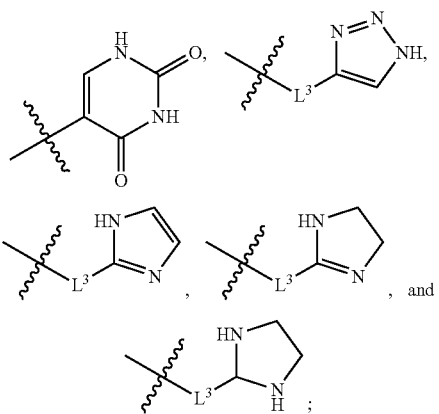

wherein each occurrence of $L^3$ is independently selected from the group consisting of a bond and methylene.

Embodiment 5 provides a compound of any of Embodiments 1-4, wherein $R^1$ is selected from the group consisting of: phenyl, pyridinyl, pyrimidinyl, isoxazolyl,

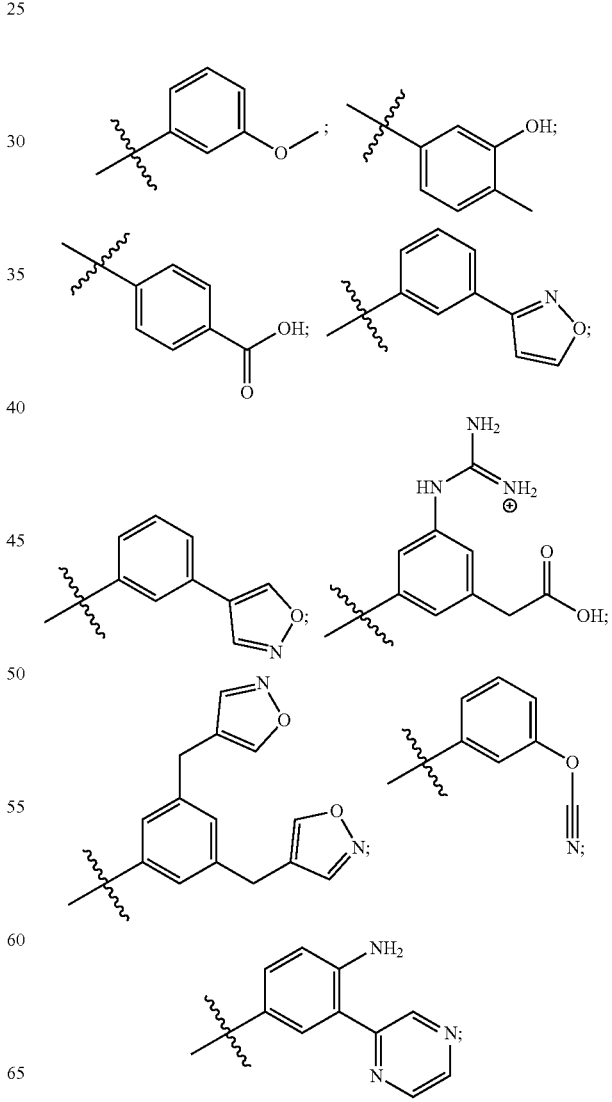

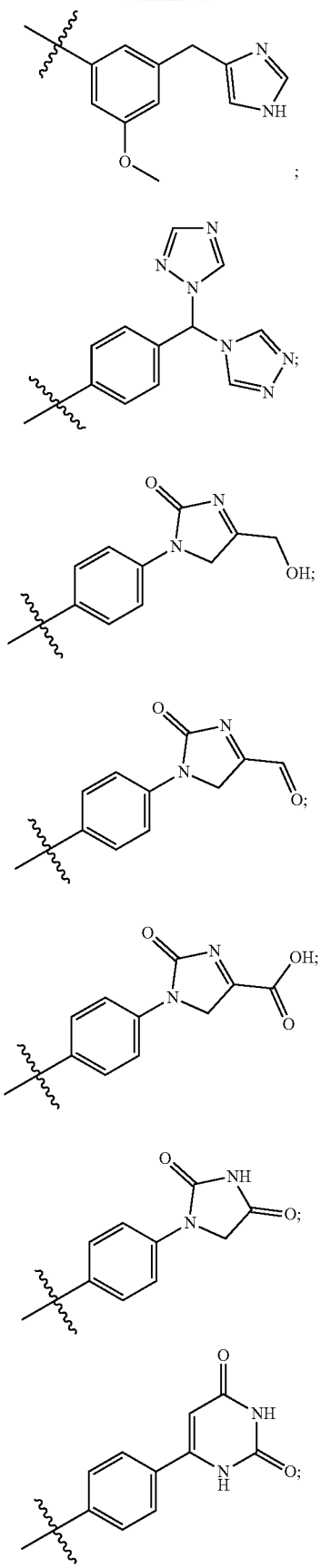

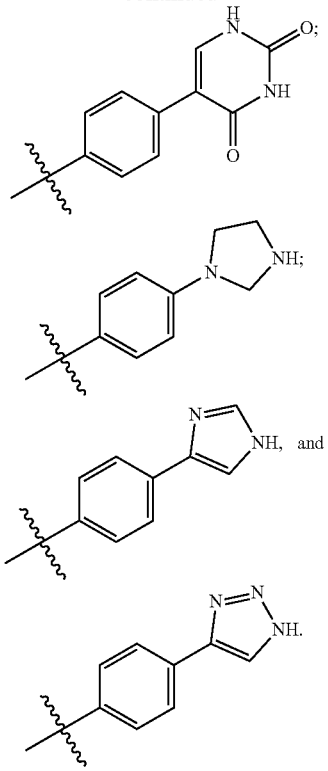

Embodiment 6 provides a compound of any of Embodiments 1-5, which is selected from the group consisting of: amino(6-(3-(isoxazol-4-yl)benzamido)naphthalen-2-yl)methaniminium; amino(6-(4-amino-3-(pyrazin-2-yl)benzamido)naphthalen-2-yl)methaniminium; (6-(3-((1H-imidazol-4-yl)methyl)-5-methoxybenzamido)naphthalen-2-yl)(amino)methaniminium; amino(6-(3-((amino(iminio)methyl)amino)-5-(carboxymethyl)benzamido)naphthalen-2-yl)methaniminium; amino(6-(2-phenylacetamido)naphthalen-2-yl)methaniminium; amino(6-(2-(pyridin-3-yl)acetamido)naphthalen-2-yl)methaniminium; amino(6-(2-(4-carboxyphenyl)acetamido)naphthalen-2-yl)methaniminium; amino(6-(2-(3-(isoxazol-4-yl)phenyl)acetamido)naphthalen-2-yl)methaniminium; (6-(2-(3-((1H-imidazol-4-yl)methyl)-5-methoxyphenyl)acetamido)naphthalen-2-yl)(amino)methaniminium; amino(6-(2-(3-hydroxy-4-methylphenyl)-2-methylpropanamido)naphthalen-2-yl)methaniminium; amino(6-(3-(pyridin-3-yl)propanamido)naphthalen-2-yl)methaniminium; amino(6-((isoxazol-4-ylmethyl)carbamoyl)naphthalen-2-yl)methaniminium; amino(6-((2-(isoxazol-4-yl)ethyl)carbamoyl)naphthalen-2-yl)methaniminium; amino(6-((3-(isoxazol-3-yl)phenyl)carbamoyl)naphthalen-2-yl)methaniminium; amino((3-(6-(amino(iminio)methyl)-2-naphthamido)-5-(carboxymethyl)phenyl)amino)methaniminium; amino(6-((3,5-bis(isoxazol-4-ylmethyl)phenyl)carbamoyl)naphthalen-2-yl)methaniminium; amino(6-((4-carboxybenzyl)carbamoyl)naphthalen-2-yl)methaniminium; amino(6-(3-cyanatophenyl)naphthalen-2-yl)methaniminium; amino(6-(3-(isoxazol-3-yl)phenyl)naphthalen-2-yl)methaniminium; amino(6-(3-(isoxazol-4-yl)phenyl)naphthalen-2-yl)methaniminium; amino(6-(4-(di(1H-1,2,4-triazol-1-yl)methyl)phenyl)naphthalen-2-yl)methaniminium; amino(6-(4-(4-(hydroxymethyl)-2-oxo-2,5-dihydro-1H-imidazol-1-yl)phenyl)naphthalen-2-yl)methaniminium; amino(3-(4-(4-

(hydroxymethyl)-2-oxo-2,5-dihydro-1H-imidazol-1-yl)phenyl)isoquinolin-7-yl)methaniminium; amino(6-(4-(4-carboxy-2-oxo-2,5-dihydro-1H-imidazol-1-yl)phenyl)naphthalen-2-yl)methaniminium; amino(3-(4-(4-(hydroxymethyl)-2-oxo-2,5-dihydro-1H-imidazol-1-yl)phenyl)isoquinolin-7-yl)methaniminium; amino(3-(4-(4-formyl-2-oxo-2,5-dihydro-1H-imidazol-1-yl)phenyl)isoquinolin-7-yl)methaniminium; amino(3-(4-(4-carboxy-2-oxo-2,5-dihydro-1H-imidazol-1-yl)phenyl)isoquinolin-7-yl)methaniminium; amino(6-((4-(4-(hydroxymethyl)-2-oxo-2,5-dihydro-1H-imidazol-1-yl)phenyl)carbamoyl)naphthalen-2-yl)methaniminium; amino(3-((4-(4-(hydroxymethyl)-2-oxo-2,5-dihydro-1H-imidazol-1-yl)phenyl)carbamoyl)isoquinolin-7-yl)methaniminium; amino(6-(4-(4-(hydroxymethyl)-2-oxo-2,5-dihydro-1H-imidazol-1-yl)benzamido)naphthalen-2-yl)methaniminium; amino(3-(4-(4-(hydroxymethyl)-2-oxo-2,5-dihydro-1H-imidazol-1-yl)benzamido)isoquinolin-7-yl)methaniminium; amino(6-(4-(4-formyl-2-oxo-2,5-dihydro-1H-imidazol-1-yl)benzamido)naphthalen-2-yl)methaniminium; amino(3-(4-(4-formyl-2-oxo-2,5-dihydro-1H-imidazol-1-yl)benzamido)isoquinolin-7-yl)methaniminium; amino(6-((4-(4-formyl-2-oxo-2,5-dihydro-1H-imidazol-1-yl)phenyl)carbamoyl)naphthalen-2-yl)methaniminium; amino(3-((4-(4-formyl-2-oxo-2,5-dihydro-1H-imidazol-1-yl)phenyl)carbamoyl)isoquinolin-7-yl)methaniminium; amino(6-((4-(4-carboxy-2-oxo-2,5-dihydro-1H-imidazol-1-yl)phenyl)carbamoyl)naphthalen-2-yl)methaniminium; amino(3-((4-(4-carboxy-2-oxo-2,5-dihydro-1H-imidazol-1-yl)phenyl)carbamoyl)isoquinolin-7-yl)methaniminium; amino(6-(4-(4-carboxy-2-oxo-2,5-dihydro-1H-imidazol-1-yl)benzamido)naphthalen-2-yl)methaniminium; amino(3-(4-(4-carboxy-2-oxo-2,5-dihydro-1H-imidazol-1-yl)benzamido)isoquinolin-7-yl)methaniminium; amino(6-(4-(2,4-dioxoimidazolidin-1-yl)benzamido)naphthalen-2-yl)methaniminium; amino(3-(4-(2,4-dioxoimidazolidin-1-yl)benzamido)isoquinolin-7-yl)methaniminium; amino(6-((4-(2,4-dioxoimidazolidin-1-yl)phenyl)carbamoyl)naphthalen-2-yl)methaniminium; and amino(3-((4-(2,4-dioxoimidazolidin-1-yl)phenyl)carbamoyl)isoquinolin-7-yl)methaniminium.

Embodiment 7 provides a pharmaceutical composition comprising the compound of any of Embodiments 1-6, further comprising at least one pharmaceutically acceptable carrier.

Embodiment 8 provides the pharmaceutical composition of Embodiment 7, further comprising at least one additional therapeutic agent.

Embodiment 9 provides the pharmaceutical composition of Embodiment 8, wherein the at least one additional therapeutic agent is an antiviral agent.

The disclosures of each and every patent, patent application, and publication cited herein are hereby incorporated herein by reference in their entirety. Whereas this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:
1. A compound of Formula (I), or a salt, solvate, enantiomer, diastereoisomer, or tautomer thereof:

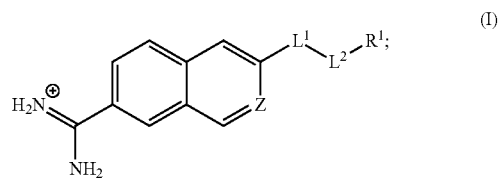

wherein:
L$^1$ is selected from the group consisting of a bond (absent),

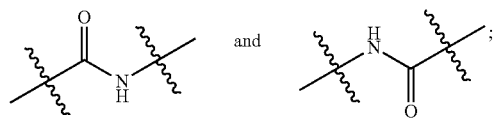 [SMILES: *NC(*)=O ; *NC(*)=O]

L$^2$ is selected from the group consisting of a bond (absent) and C$_1$-C$_6$ alkylene;
R$^1$ is selected from the group consisting of

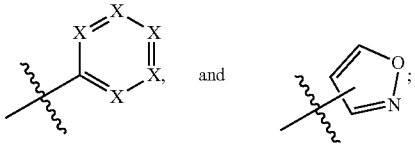

Z is selected from the group consisting of CH and N;
each instance of X is independently selected from the group consisting of CR$^2$ and N, with the proviso that 0-2 instances of X are N;
one instance of R$^2$ is selected from the group consisting of

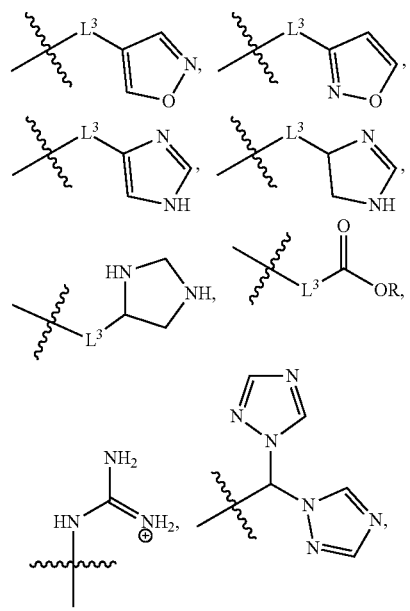

-continued

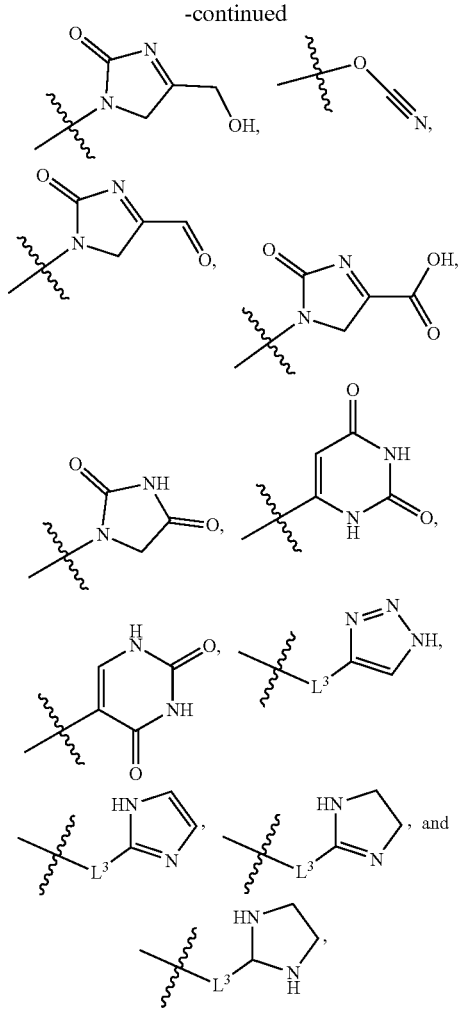

wherein each occurrence of $L^3$ is independently selected from the group consisting of a bond and methylene;

the remaining occurrences of $R^2$ are independently selected from the group consisting of H, —CN, —OH, —NRR, F, Cl, Br, I, optionally substituted $C_{1-6}$ alkyl, optionally substituted $C_{1-6}$ alkoxy, optionally substituted $C_{3-8}$ cycloalkyl, optionally substituted phenyl, optionally substituted heteroaryl, optionally substituted heterocyclyl, —(CH$_2$)$_{0-3}$C(=O)OR, —(CH$_2$)$_{0-3}$C(=O)NRR, —(CH$_2$)$_{0-3}$NRRR, and —N(R)—C(=N$^+$RR)—NRR; and each occurrence of R is independently selected from the group consisting of H and $C_1$-$C_6$ alkyl.

2. The compound of claim 1, wherein each occurrence of heteroaryl or heterocyclyl is independently selected from the group consisting of pyridyl, pyrimidinyl, pyrazinyl, isoxazolyl, oxazolyl, thiazolyl, imidazolyl, imidazolidin-2-one-1-yl, 1,5-dihydro-2H-imidazol-2-one-1-yl, 2-pyrazolyl, 1,2,3-triazolyl, 1,2,4-triazolyl, uracil, thyminyl, pyranyl, furanyl, and hydantoinyl.

3. The compound of claim 1, wherein each occurrence of alkyl, alkoxy, cycloalkyl, phenyl, heteroaryl, or heterocyclyl is independently optionally substituted with at least one group selected from the group consisting of —CN, —OR', —NR'R', F, Cl, Br, I, $C_{1-6}$ alkyl, $C_{3-8}$ cycloalkyl, phenyl, heteroaryl, and heterocyclyl, wherein each occurrence of R' is independently selected from the group consisting of H and $C_1$-$C_6$ alkyl.

4. The compound of claim 1, wherein $R^1$ is selected from the group consisting of: isoxazolyl

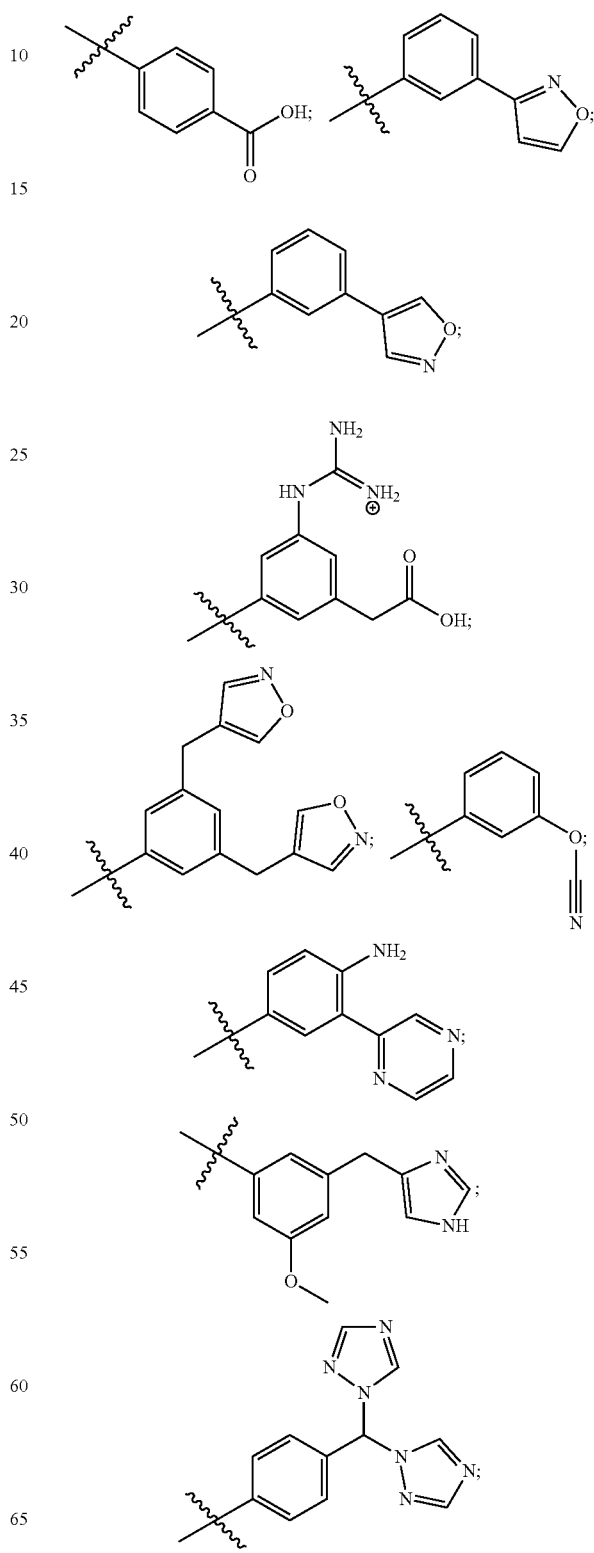

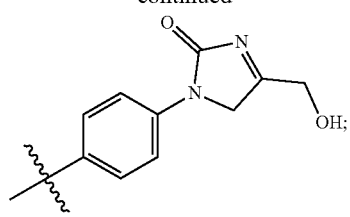
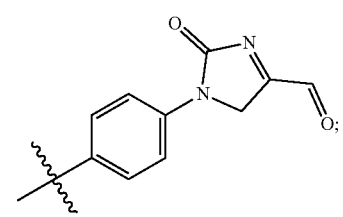
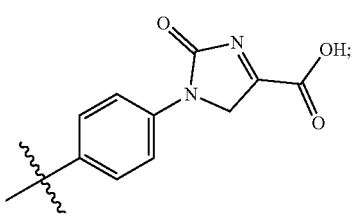
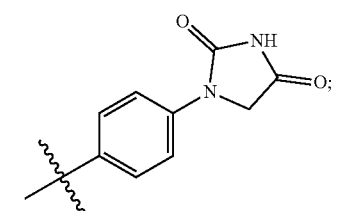
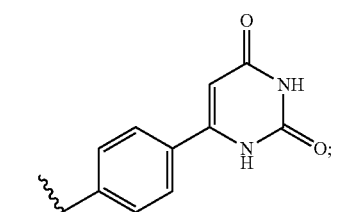
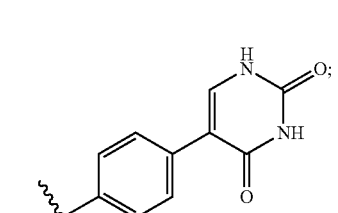
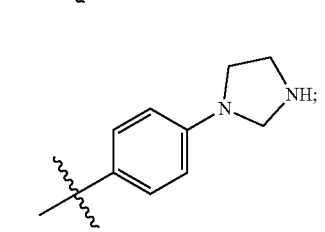
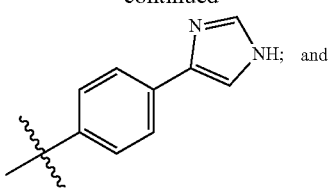
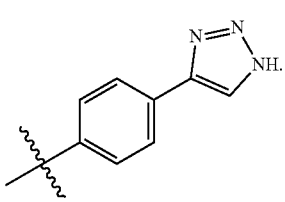
5. A compound selected from the group consisting of:
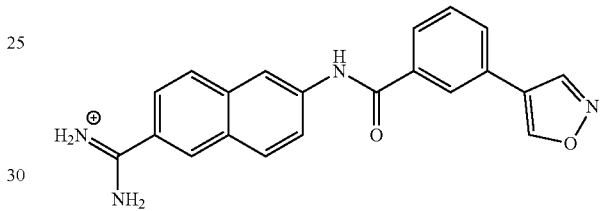
amino(6-(3-(isoxazol-4-yl)benzamido)naphthalen-2-yl)methaniminium;
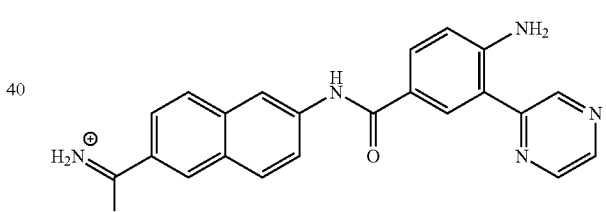
amino(6-(4-amino-3-(pyrazin-2-yl)benzamido)naphthalen-2-yl)methaniminium;
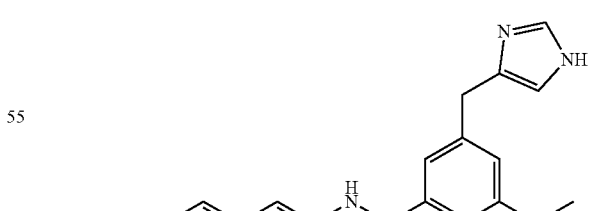
(6-(3-(1H-imidazol-4-yl)methyl)-5-methoxybenzamido)naphthalen-2-yl)(amino)methaniminium;

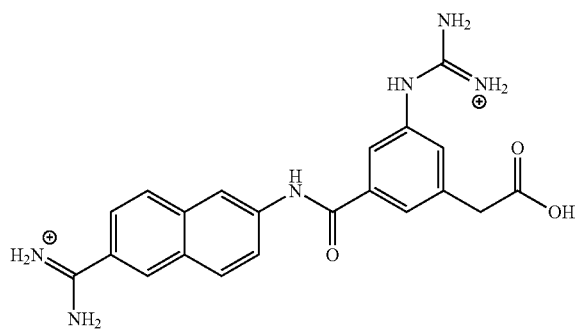 [SMILES: NC(=[NH2+])Nc1cc(CC(=O)O)cc(C(=O)Nc2ccc3cc(C(N)=[NH2+])ccc3c2)c1]

amino(6-(3-((amino(iminio)methyl)amino)-5-(carboxymethyl)benzamido)naphthalen-2-yl)methaniminium;

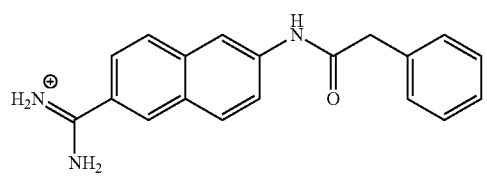 [SMILES: NC(=[NH2+])c1ccc2cc(NC(=O)Cc3ccccc3)ccc2c1]

amino(6-(2-phenylacetamido)naphthalen-2-yl)methaniminium;

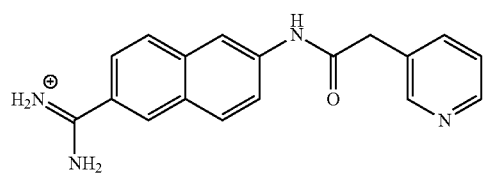

amino(6-(2-(pyridin-3-yl)acetamido)naphthalen-2-yl)methaniminium;

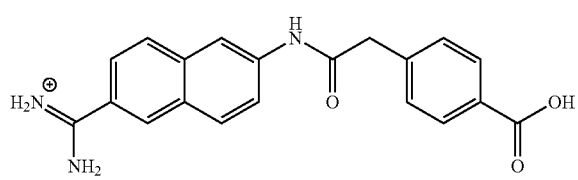 [SMILES: NC(=[NH2+])c1ccc2cc(NC(=O)Cc3ccc(C(=O)O)cc3)ccc2c1]

amino(6-(2-(4-carboxyphenyl)acetamido)naphthalen-2-yl)methaniminium;

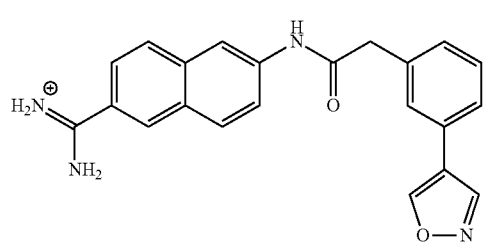 [SMILES: NC(=[NH2+])c1ccc2cc(NC(=O)Cc3cccc(-c4cnoc4)c3)ccc2c1]

amino(6-(2-(3-(isoxazol-4-yl)phenyl)acetamido)naphthalen-2-yl)methaniminium;

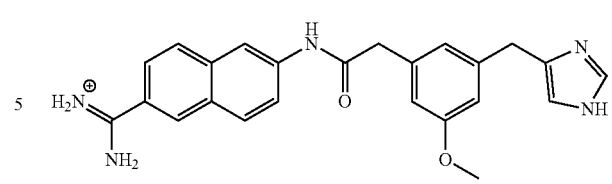

(6-(2-(3-(1H-imidazol-4-yl)methyl)-5-methoxyphenyl)acetamido)naphthalen-2-yl)(amino)methaniminium;

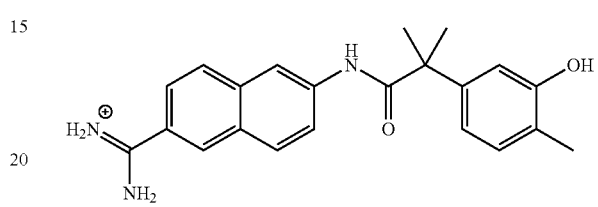

amino(6-(2-(3-hydroxy-4-methylphenyl)-2-methylpropanamido)naphthalen-2-yl)methaniminium;

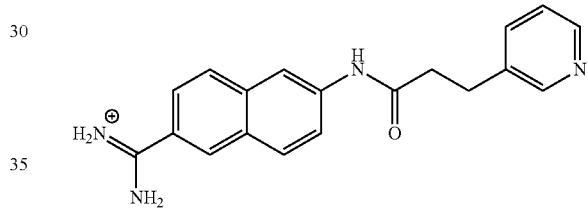

amino(6-(3-(pyridin-3-yl)propanamido)naphthalen-2-yl)methaniminium;

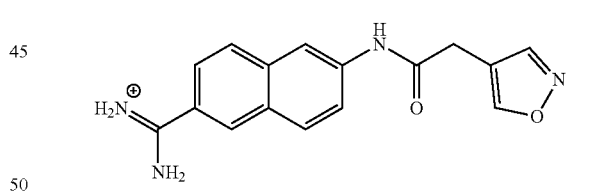

amino(6-((isoxazol-4-ylmethyl)carbamoyl)naphthalen-2-yl)methaniminium;

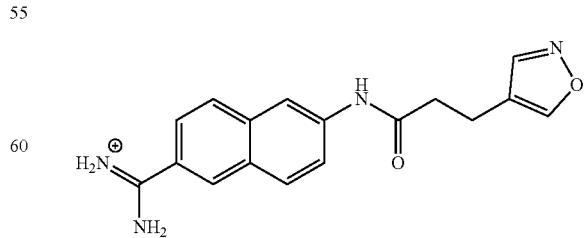

amino(6-((2-(isoxazol-4-yl)ethyl)carbamoyl)naphthalen-2-yl)methaniminium;

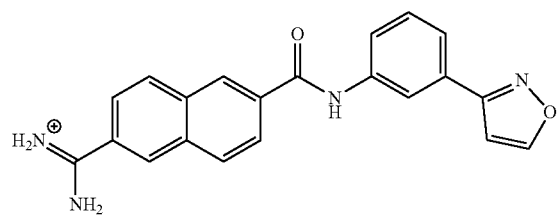 [SMILES: NC(=[NH2+])c1ccc2cc(C(=O)Nc3cccc(-c4ccon4)c3)ccc2c1]

amino(6-((3-(isoxazol-3-yl)phenyl)carbamoyl)naphthalen-2-yl)methaniminium;

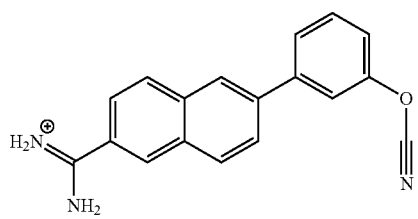

amino(6-(3-cyanatophenyl)naphthalen-2-yl)methaniminium;

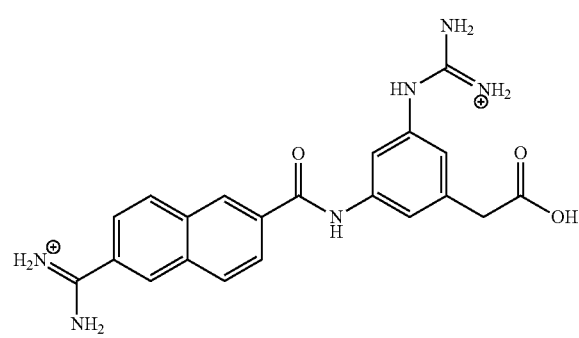 [SMILES: NC(=[NH2+])Nc1cc(CC(=O)O)cc(NC(=O)c2ccc3cc(C(N)=[NH2+])ccc3c2)c1]

amino((3-(6-(amino(iminio)methyl)-2-naphthamido)-5-(carboxymethyl)phenyl)amino)methaniminium;

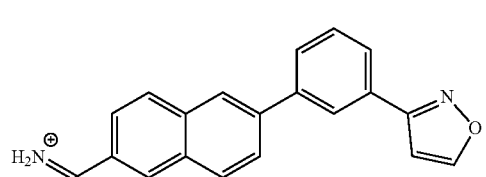

amino(6-(3-(isoxazol-3-yl)phenyl)naphthalen-2-yl)methaniminium;

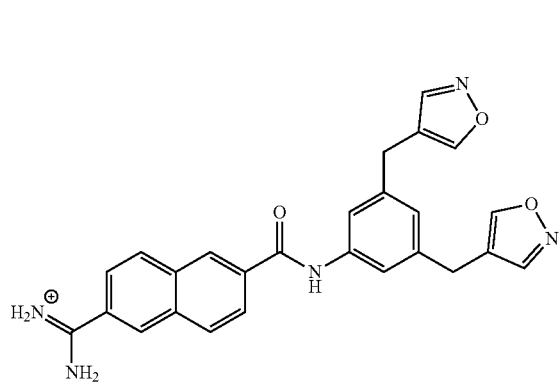 [SMILES: NC(=[NH2+])c1ccc2cc(C(=O)Nc3cc(Cc4cnoc4)cc(Cc4cnoc4)c3)ccc2c1]

amino(6-((3,5-bis(isoxazol-4-ylmethyl)phenyl)carbamoyl)naphthalen-2-yl)methaniminium;

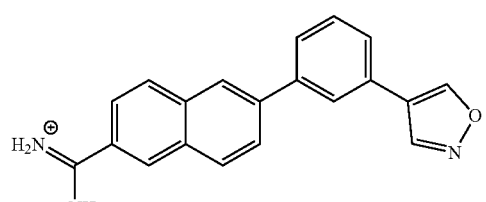

amino(6-(3-(isoxazol-4-yl)phenyl)naphthalen-2-yl)methaniminium;

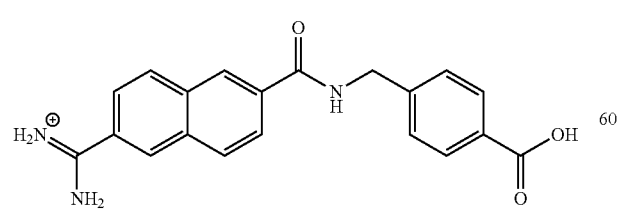

amino(6-((4-carboxybenzyl)carbamoyl)naphthalen-2-yl)methaniminium;

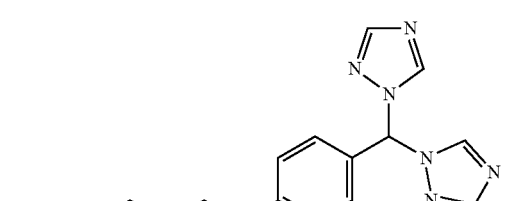

amino(6-(4-(di(1H-1,2,4-triazol-1-yl)methyl)phenyl)naphthalen-2-yl)methaniminium;

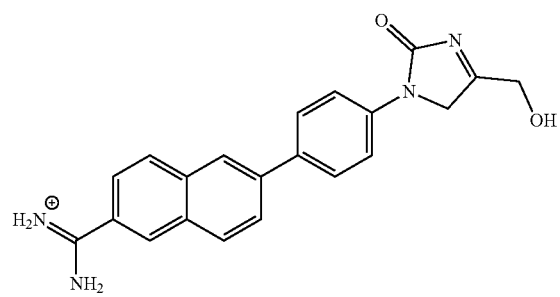 [SMILES: NC(=[NH2+])c1ccc2cc(-c3ccc(N4CC(CO)=NC4=O)cc3)ccc2c1]

amino(6-(4-(4-(hydroxymethyl)-2-oxo-2,5-dihydro-1H-imidazol-1-yl)phenyl)naphthalen-2-yl)methaniminium;

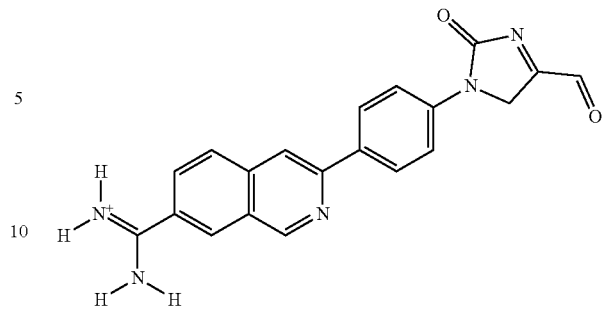

amino(3-(4-(4-formyl-2-oxo-2,5-dihydro-1H-imidazol-1-yl)phenyl)isoquinolin-7-yl)methaniminium;

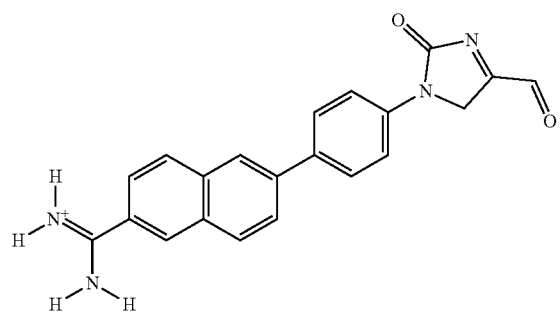 [SMILES: NC(=[NH2+])c1ccc2cc(-c3ccc(N4CC(C=O)=NC4=O)cc3)ccc2c1]

amino(3-(4-(4-(hydroxymethyl)-2-oxo-2,5-dihydro-1H-imidazol-1-yl)phenyl)isoquinolin-7-yl)methaniminium;

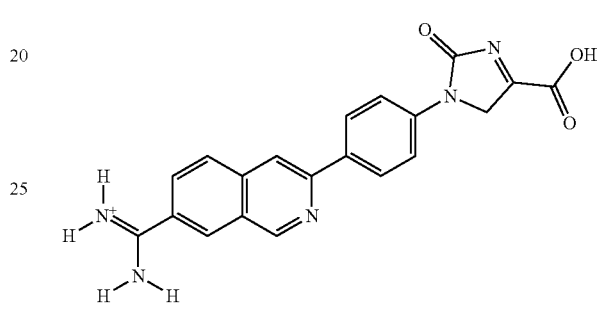

amino(3-(4-(4-carboxy-2-oxo-2,5-dihydro-1H-imidazol-1-yl)phenyl)isoquinolin-7-yl)methaniminium;

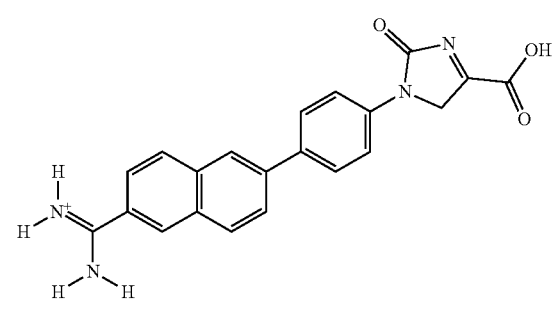 [SMILES: NC(=[NH2+])c1ccc2cc(-c3ccc(N4CC(C(=O)O)=NC4=O)cc3)ccc2c1]

amino(6-(4-(4-carboxy-2-oxo-2,5-dihydro-1H-imidazol-1-yl)phenyl)naphthalen-2-yl)methaniminium;

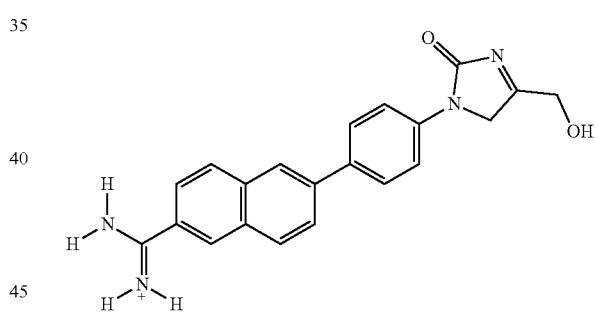

amino(6-((4-(4-(hydroxymethyl)-2-oxo-2,5-dihydro-1H-imidazol-1-yl)phenyl)carbamoyl)naphthalen-2-yl)methaniminium;

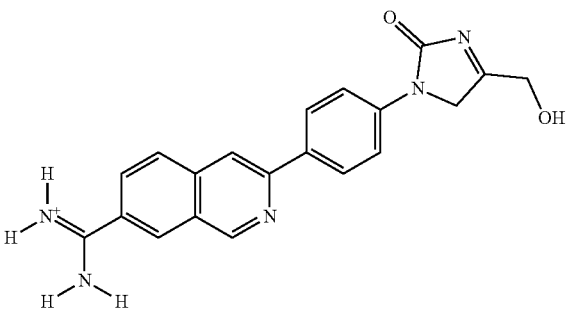 [SMILES: NC(=[NH2+])c1ccc2cc(-c3ccc(N4CC(CO)=NC4=O)cc3)ncc2c1]

amino(3-(4-(4-(hydroxymethyl)-2-oxo-2,5-dihydro-1H-imidazol-1-yl)phenyl)isoquinolin-7-yl)methaniminium;

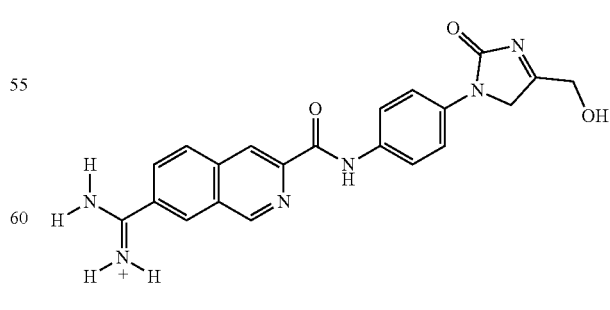

amino(3-((4-(4-(hydroxymethyl)-2-oxo-2,5-dihydro-1H-imidazol-1-yl)phenyl)carbamoyl)isoquinolin-7-yl)methaniminium;

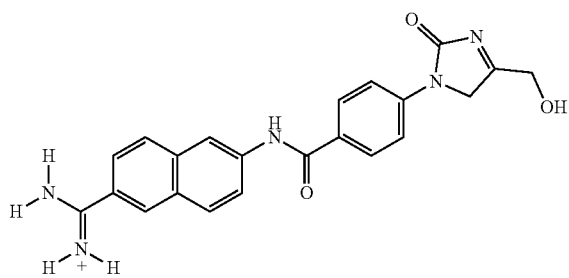

amino(6-(4-(4-(hydroxymethyl)-2-oxo-2,5-dihydro-1H-imidazol-1-yl)benzamido)naphthalen-2-yl)methaniminium;

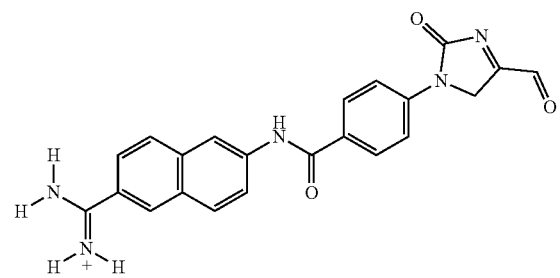

amino(6-((4-(4-formyl-2-oxo-2,5-dihydro-1H-imidazol-1-yl)phenyl)carbamoyl)naphthalen-2-yl)methaniminium;

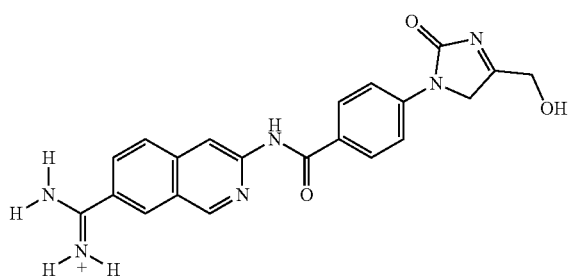

amino(3-(4-(4-(hydroxymethyl)-2-oxo-2,5-dihydro-1H-imidazol-1-yl)benzamido)isoquinolin-7-yl)methaniminium;

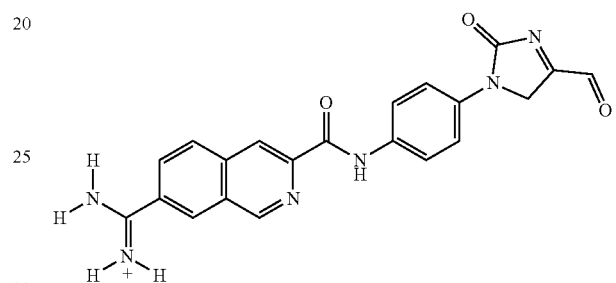

amino(3-((4-(4-formyl-2-oxo-2,5-dihydro-1H-imidazol-1-yl)phenyl)carbamoyl)isoquinolin-7-yl)methaniminium;

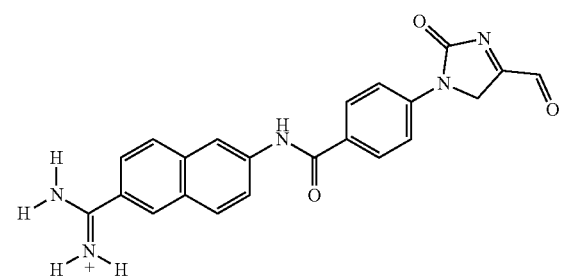

amino(6-(4-(4-formyl-2-oxo-2,5-dihydro-1H-imidazol-1-yl)benzamido)naphthalen-2-yl)methaniminium;

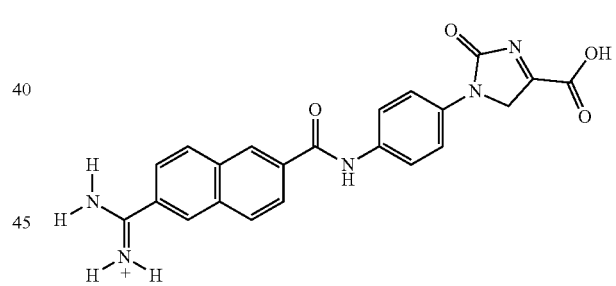

amino(6-((4-(4-carboxy-2-oxo-2,5-dihydro-1H-imidazol-1-yl)phenyl)carbamoyl)naphthalen-2-yl)methaniminium;

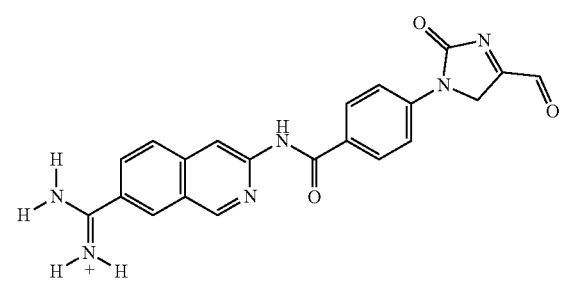

amino(3-(4-(4-formyl-2-oxo-2,5-dihydro-1H-imidazol-1-yl)benzamido)isoquinolin-7-yl)methaniminium;

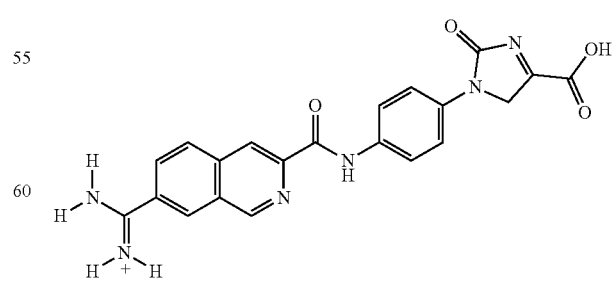

amino(3-((4-(4-carboxy-2-oxo-2,5-dihydro-1H-imidazol-1-yl)phenyl)carbamoyl)isoquinolin-7-yl)methaniminium;

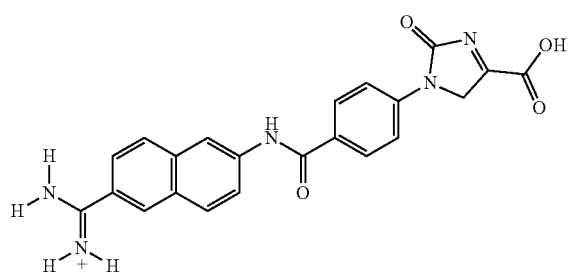

amino(6-(4-(4-carboxy-2-oxo-2,5-dihydro-1H-imidazol-1-yl)benzamido)naphthalen-2-yl)methaniminium;

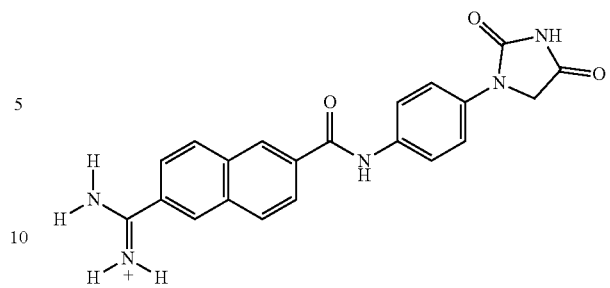

amino(6-((4-(2,4-dioxoimidazolidin-1-yl)phenyl)carbamoyl)naphthalen-2-yl)methaniminium; and

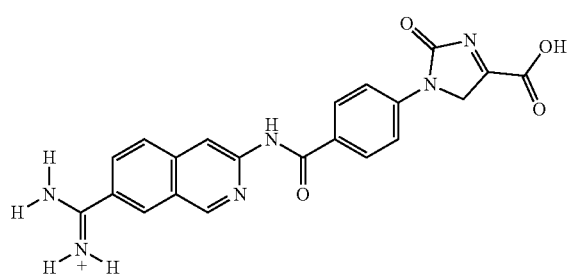

amino(3-(4-(4-carboxy-2-oxo-2,5-dihydro-1H-imidazol-1-yl)benzamido)isoquinolin-7-yl)methaniminium;

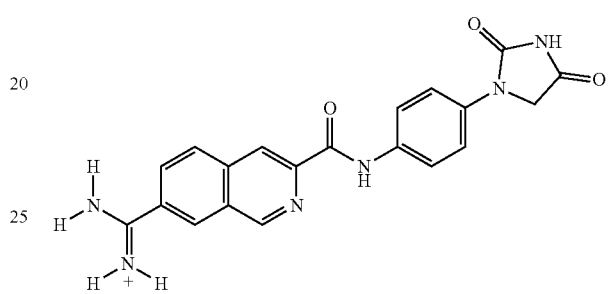

amino(3-((4-(2,4-dioxoimidazolidin-1-yl)phenyl)carbamoyl)isoquinolin-7-yl)methaniminium,
or a salt, solvate, or tautomer thereof.

6. A pharmaceutical composition comprising the compound of claim 5, further comprising at least one pharmaceutically acceptable carrier.

7. The pharmaceutical composition of claim 6, further comprising at least one additional therapeutic agent.

8. The pharmaceutical composition of claim 7, wherein the at least one additional therapeutic agent is an antiviral agent.

9. A method of inhibiting a type II transmembrane serine protease (TTSP), the method comprising contacting the TTSP with at least one compound of claim 5.

10. The method of claim 9, wherein the TTSP comprises target transmembrane protease serine 11E (DESC1).

11. A method of inhibiting cleavage of hemagglutinin (HA) by a type II transmembrane serine proteases (TTSP) in an influenza virus, the method comprising contacting the TTSP with at least one compound of claim 5.

12. The method of claim 11, wherein the TTSP comprises target transmembrane protease serine 11E (DESC1).

13. The method of claim 11, wherein the subject is a mammal or a bird.

14. The method of claim 11, wherein the subject is a human.

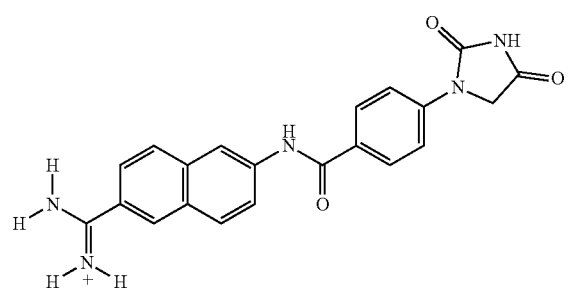

amino(6-(4-(2,4-dioxoimidazolidin-1-yl)benzamido)naphthalen-2-yl)methaniminium;

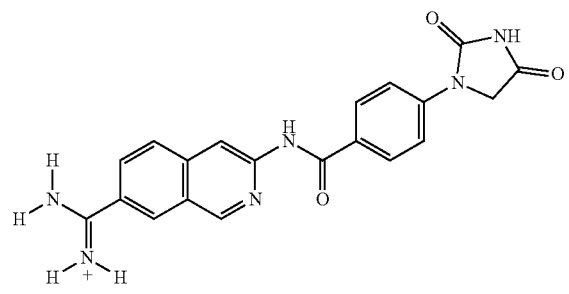

amino(3-(4-(2,4-dioxoimidazolidin-1-yl)benzamido)isoquinolin-7-yl)methaniminium;

15. A method of treating an infection by a influenza virus in a subject in need thereof, the method comprising administering to the subject a therapeutically effective amount of the compound of claim 5.

16. The method of claim 15, wherein the influenza virus comprises an influenza A virus.

17. The method of claim 15, wherein the subject is a mammal or a bird.

18. The method of claim 15, wherein the subject is a human.

* * * * *